(12) United States Patent
Krolewski et al.

(10) Patent No.: US 10,953,035 B2
(45) Date of Patent: Mar. 23, 2021

(54) COMPOSITIONS AND METHODS FOR TREATING AND PREVENTING END STAGE RENAL DISEASE

(71) Applicant: Joslin Diabetes Center, Inc., Boston, MA (US)

(72) Inventors: Andrzej Krolewski, Needham, MA (US); Marcus Pezzolesi, Lunenburg, MA (US)

(*) Notice: Subject to any disclaimer, the term of this patent is extended or adjusted under 35 U.S.C. 154(b) by 0 days.

(21) Appl. No.: 16/171,952

(22) Filed: Oct. 26, 2018

(65) Prior Publication Data

US 2019/0183919 A1 Jun. 20, 2019

Related U.S. Application Data

(63) Continuation of application No. PCT/US2017/030122, filed on Apr. 28, 2017.

(60) Provisional application No. 62/329,079, filed on Apr. 28, 2016.

(51) Int. Cl.
| | |
|---|---|
| *A61K 31/7105* | (2006.01) |
| *C12Q 1/6883* | (2018.01) |
| *A61K 45/06* | (2006.01) |
| *A61P 13/12* | (2006.01) |
| *G01N 33/70* | (2006.01) |

(52) U.S. Cl.
CPC .......... *A61K 31/7105* (2013.01); *A61K 45/06* (2013.01); *A61P 13/12* (2018.01); *C12Q 1/6883* (2013.01); *G01N 33/70* (2013.01); *C12Q 2600/158* (2013.01); *C12Q 2600/178* (2013.01); *G01N 2800/347* (2013.01); *G01N 2800/50* (2013.01); *G01N 2800/52* (2013.01); *G01N 2800/54* (2013.01); *G01N 2800/56* (2013.01)

(58) Field of Classification Search
None
See application file for complete search history.

(56) References Cited

PUBLICATIONS

Pezzolesi, MG et al., "Circulating TGF-beta1-Regulated miRNAs and the Risk of Rapid Progression to ESRD in Type 1 Diabetes, Diabetes," Apr. 30, 2015, vol. 64: No. 9.
Rosolowsky, ET et al., "Risk for ESRD in type 1 diabetes remains high despite renoprotection." Journal of the American Society of Nephrology. Mar. 2011, vol. 22: No. 3.
Trionfini, P. et al., MicroRNAs in kidney physiology and disease. Nature Reviews Nephrology. Jan. 2015, vol. 11, No. 1.
International Seach Report relating to PCT/US17/30122, completed on Jul. 8, 2017 and dated Aug. 11, 2017.
International Preliminary Report of Patentability related to PCT/US2017/030122, completed on Jul. 8, 2017 and dated Aug. 11, 2017.
Written Opinion of the International Searching Authority relating to PCT/US17/30122, completed Jul. 8, 2017 and dated Aug. 11, 2017.

*Primary Examiner* — Tracy Vivlemore
(74) *Attorney, Agent, or Firm* — Womble Bond Dickinson (US) LLP; Cristin Cowles; Kevin Fiala

(57) ABSTRACT

The invention provides methods for preventing end stage renal disease (ESRD) in subjects having a disorder associated with chronic kidney failure, such as diabetes or high blood pressure. Also included are markers (miRNAs) that may be used to identify subjects who are at risk of developing ESRD.

12 Claims, 1 Drawing Sheet
Specification includes a Sequence Listing.

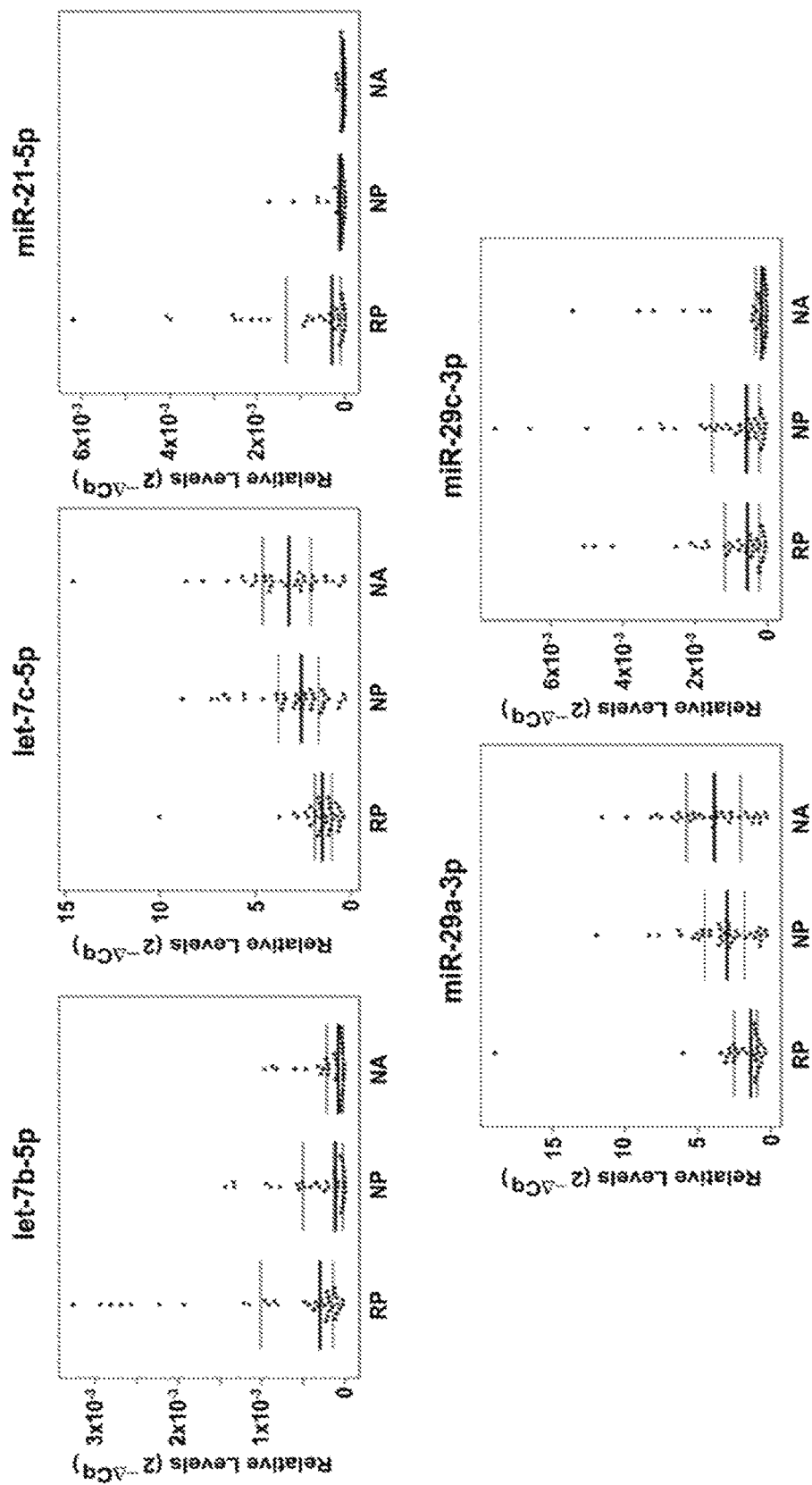

COMPOSITIONS AND METHODS FOR TREATING AND PREVENTING END STAGE RENAL DISEASE

RELATED APPLICATIONS

This application is a Continuation of International Patent Application No. PCT/US2017/030122, filed Apr. 28, 2017, which claims priority to U.S. Provisional Patent Application No. 62/329,079 filed on Apr. 28, 2016, and entitled "Compositions And Methods For Treating And Preventing End Stage Renal Disease." Each of the foregoing applications is incorporated herein by reference in its entirety.

GOVERNMENT SUPPORT

This invention was made with government support under Grant #R01 DK041526-23 awarded by the National Institutes of Health/National Institute of Diabetes and Digestive and Kidney Diseases, and Grant #13GHSU300 (U24 DK076169-08) awarded by the National Institute of Diabetes and Digestive and Kidney Diseases Diabetic Complications Consortium (DiaComp). The government has certain rights in the invention.

SEQUENCE LISTING

The instant application contains a Sequence Listing which has been submitted electronically in ASCII format and is hereby incorporated by reference in its entirety. Said ASCII copy, created on Oct. 25, 2018, is named J103021_1040 US.PCT_Sequence_Listing.txt and is 4,203 bytes in size.

BACKGROUND

End stage renal disease (ESRD), also referred to as end stage kidney disease, is the last stage of chronic kidney disease. ESRD occurs when a person's kidneys can no longer support their body's needs. The kidneys remove waste and excess water from the body. ESRD almost always comes after chronic kidney disease. The kidneys may slowly stop working over 10 to 20 years before end-stage disease results.

Diabetes is a common cause of ESRD. Diabetic nephropathy (DN) is characterized by a series of structural abnormalities affecting the function of the kidney (1). In addition to renal cell hypertrophy and glomerular basement membrane thickening, the accumulation of extracellular matrix (ECM) proteins and mesangial cell expansion are all key features of this disease that promote renal fibrosis (1). These structural changes lead to two separable clinical manifestations; increased urinary albumin excretion and the progressive decline of renal function (2). For 10-15% of all patients diagnosed with type 1 diabetes (T1D), it is this latter feature of this process that ultimately culminates in the onset of ESRD (2).

Transforming growth factor-beta 1 (TGF-β1), a multifunctional cytokine, is an essential mediator of the pathogenesis of DN (3; 4). In the setting of diabetes, high glucose levels stimulate the renal production of TGF-β1 and set in motion a signaling cascade that promotes fibrogenesis (5). During this process, TGF-β1 exerts its effects by up-regulating several pro-fibrotic factors, including various collagen genes, through activation of the Smad and mitogen-activated protein kinase (MAPK) signaling pathways (6-9). Recently, in vitro and in vivo models of DN have shown that TGF-β1 also positively or negatively regulates the expression of several microRNAs (miRNAs) that, in turn, amplify TGF-β1-signaling to further promote renal fibrosis (10-18). These studies clearly demonstrate that TGF-β1-regulated miRNAs are key downstream regulators of the TGF-β/Smad signaling pathway and, therefore, are important modulators of diabetic kidney disease.

miRNAs are small, non-coding RNAs that are involved in regulating gene expression through different mechanisms, including translational repression. miRNAs are initially transcribed from DNA as lengthy primary miRNA transcripts ("pri-miRNAs"), ranging in size from hundreds to thousands of nucleotides. Pri-miRNA is processed in the nucleus by the enzyme complex Drosha-DGCR8 to form stem-loop precursor miRNA ("pre-miRNAs"). Pre-miRNA is transported to the cytoplasm by the protein exportin 5, where it is cleaved by the enzyme Dicer to generate mature (functional) miRNA. The human genome encodes over 1300 miRNAs, which have been cataloged at "miRBase: The microRNA Database" (http://www.mirbase.org/). miRNA expression has been reported in a wide array of cell and tissue types, and extracellularly, e.g., in biological fluids.

miRNAs have been found to be detectable in a variety of human body fluids, including blood, saliva, and urine (19; 20). miRNAs that are present in the circulation, including those in plasma and serum, are protected from endogenous ribonuclease activity, allowing them to remain remarkably stable. Because of this, circulating miRNAs hold great promise to serve as potentially useful biomarkers to monitor pathophysiological changes and the prognosis disease (19; 21; 22). Moreover, because the deregulation of miRNAs also contributes to the development of various human diseases, these molecules are becoming attractive targets for miRNA-based therapeutic interventions (23).

For example, miR-29a-3p was found to be protective against the loss of renal function in patients from our study. Previous studies have shown that miR-29a-3p is down-regulated in response to TGF-β1 in a variety of human and non-human cell lines, including human and rat proximal tubule epithelial cells, mouse mesangial cells, and human podocytes (10; 40; 43). miR-29a and other members of the miR-29 family negatively regulate the expression of several fibrotic genes, including a number of collagen genes (e.g., COL1A1 and COL1A2 and collagen type IV, alpha1, 2, and 3), via a Smad3-dependent mechanism (10; 40; 41; 43). In addition to these in vitro models, and in agreement with our observation in patients at risk of renal function decline, miR-29a has also been shown to be markedly decreased in kidney tissue in rodent models of diabetic renal fibrosis (10; 43). Similar findings have also been noted in non-diabetic mouse models, suggesting that aberrant miR-29 levels are common to both diabetic and non-diabetic kidney disease (10; 43).

Interestingly, miR-29c expression has been shown to be increased in both in vitro and in vivo models of DN (48). As demonstrated by Long et al., miR-29c levels are significantly increased in kidney glomeruli from db/db diabetic mice compared to control db/m littermates. Moreover, miR-29c expression is also significantly increased in both kidney podocytes and kidney microvascular endothelial cells in response to hyperglycemic conditions. Importantly, in contrast to control db/db mice, Long et al. further demonstrated that knockdown of miR-29c with a chemically modified antisense oligonucleotide significantly reduced albuminuria in db/db mice in vivo.

Treatment for ESRD usually involves dialysis or kidney transplantation. Without dialysis or kidney transplantation, prognosis for patients having ESRD is poor, leading to death. Both dialysis and kidney transplantation, however, are complicated treatments each carrying their own risks. As such, there remains a need for methods of treating ESRD and identifying patients who may be at risk for developing ESRD in an effort to prevent this devastating disease.

SUMMARY OF THE INVENTION

The present invention is based, at least in part, on the discovery of an association between certain miRNAs and the risk for developing ESRD. Accordingly, the present disclosure provides that certain of the factors disclosed herein can be used, e.g., as biomarkers, to predict risk of developing ESRD in a subject, e.g., a subject having a disorder associated with chronic kidney failure, such as diabetes. The present disclosure also provides that certain of the factors disclosed herein can be used in the treatment or therapy of preventing or treating ESRD. Thus, the present invention provides novel miRNA biomarkers which may be used to determine a subject's risk for developing End Stage Renal Disease (ESRD). The miRNAs described herein also may be used for therapeutic purposes when their activity is increased or decreased. The miRNAs identified for use in the compositions and methods of the invention, include, but are not limited to, miR-10b-5p, miR-451a, miR-199a-5p, miR-3907, miR-143-3p, miR-19b-3p, miR-22-5p, miR-221-3p, miR-24-3p, miR-4507, miR-4539, miR-631, miR-766-3p, miR-3940-5p, miR-3200-5p, let-7c-5p, miR-29a-3p, miR-1537-3p, miR-4505, miR-93-3p, miR-15b-3p, miR-663a, let-7b-5p, miR-21-5p, miR-1909-5p, miR-4446-3p and miR-373-5p.

Accordingly, in a first aspect, the invention features a method for identifying a subject who is at risk of developing end-stage renal disease (ESRD), said method comprising determining the relative level of a progressor miRNA in a sample from the subject, wherein a higher level of the progressor miRNA in comparison to either a non-progressor control level of the progressor miRNA or a normoalbuminuric control level of the progressor miRNA indicates that the subject is at risk of developing ESRD. In one embodiment, the progressor miRNA is let-7b-5p and/or miR-21-5p. In another embodiment, the method further comprises administering to the subject an antagonist of let-7b-5p and/or miR-21-5p if the subject is at risk of developing ESRD.

In a further embodiment, the method further comprises administering to the subject a renal protective agent if the subject is at risk of developing ESRD.

In another aspect, the invention features a method for identifying a subject who is a non-progressor, said method comprising determining a relative level of a protective miRNA in a sample from a subject having a disorder associated with chronic kidney disease, wherein a comparable level of the protective miRNA relative to a normoalbuminuric control level of the protective miRNA or a higher level of the protective miRNA relative to a non-progressor control level of the protective miRNA indicates that the subject is a non-progressor. In one embodiment, the protective miRNA is let-7c-5p and/or miR-29a-3p.

In one embodiment of any of the above aspects, the subject has diabetes or high blood pressure.

In another embodiment of any of the above aspects, the sample is a plasma sample.

In a further embodiment of any of the above aspects, the level of the miRNA is determined using is determined using quantitative PCR (qPCR), hybridization, microarray or Northern blot.

In another aspect, the invention features a method of inhibiting the progression of chronic kidney disease in a subject in need thereof, said method comprising administering to the subject an effective amount of a protective miRNA agent and/or an antagonist of a progressor miRNA.

In one embodiment, the subject is an ESRD progressor. In a further embodiment, inhibition of the progression of chronic kidney disease is determined by an albumin to creatinine ratio (ACR) urine test or a glomerular filtration rate (GFR) test.

In another aspect, the invention features a method of treating ESRD in a subject comprising administering to the subject a therapeutically effective amount of a protective miRNA agent and/or an antagonist of a progressor miRNA.

In one embodiment, the protective miRNA agent is a let-7c-5p agent and/or an miR-29a-3p agent. In a further embodiment, the let-7c-5p agent is selected from the group consisting of let-7c-5p, a let-7c-5p mimic, a synthetic let-7c-5p oligonucleotide, and an expression vector encoding let-7c-5p. In another further embodiment, the miR-29a-3p agent is selected from the group consisting of miR-29a-3p, a miR-29a-3p mimic, a synthetic miR-29a-3p oligonucleotide, and an expression vector encoding miR-29a-3p In a further embodiment of any one of the above aspects or embodiments, the progressor miRNA is let-7b-5p and/or miR-21-5p. In another further embodiment of any one of the above aspects or embodiments, the antagonist is an antisense inhibitor of the progressor miRNA. In a related embodiment, the antisense inhibitor comprises a nucleic acid molecule that is at least 80% complementary to SEQ ID NO: 23 or SEQ ID NO: 24.

In a further embodiment of any one of the above aspects or embodiments, the method further comprises administering a therapeutically effective amount of a renal protective agent to the subject. In another further embodiment of any one of the above aspects or embodiments, the subject has diabetes or high blood pressure.

BRIEF DESCRIPTION OF THE DRAWINGS

FIG. 1 is a graph that shows relative levels of TGF-β1-regulated miRNAs let-7b-5p, let-7c-5p, miR-21-5p, miR-29a-3p and miR-29c-3p in plasma from rapid progressors, nonprogressors, and normoalbuminuric control subjects.

DETAILED DESCRIPTION

1. Definitions

Prior to setting forth the invention in detail, definitions of certain terms to be used herein are provided. Unless defined otherwise, all technical and scientific terms used herein have the same meaning as is commonly understood by one of skill in the art.

As used herein interchangeably, a "microRNA," "miR," or "miRNA" refers to the unprocessed (e.g., precursor) or processed (e.g., mature) RNA transcript from a miR gene. The miRNAs regulate gene expression and are encoded by genes from whose DNA they are transcribed but miRNAs are not translated into protein (i.e. miRNAs are non-coding RNAs). miRNAs are small, non-coding RNAs that are involved in regulating gene expression through different mechanisms, including translational repression. miRNAs are initially transcribed from DNA as lengthy primary miRNA transcripts ("pri-miRNAs"), ranging in size from hundreds to thousands of nucleotides. Pri-miRNA is processed in the nucleus by the enzyme complex Drosha- DGCR8 to form stem-loop precursor miRNA ("pre-miRNA"). Pre-miRNA is transported to the cytoplasm by the protein exportin 5, where it is cleaved by the enzyme Dicer to generate mature (functional) miRNA. The human genome encodes over 1300 miRNAs, which have been cataloged at "miRBase: The microRNA Database" (http://www.mirbase.org/). miRNA expression has been reported in a wide array of cell and tissue types, and extracellularly, e.g., in biological fluids.

The term "subject" or "patient," as used interchangeably herein, refers to either a human or non-human animal. In one embodiment, a subject is a human subject.

The term "sample" as used herein refers to cells or tissue obtained from a subject. The source of the tissue or cell sample may be solid tissue (as from a fresh, frozen and/or preserved organ or tissue sample or biopsy or aspirate); whole blood or any blood constituents; or bodily fluids, such as serum, plasma, urine, saliva, sweat or synovial fluid. In one embodiment, the sample is a plasma sample obtained from a human subject.

As used herein, the term "a disorder associated with chronic kidney disease" refers to a disease or condition associated with impaired kidney function which can cause kidney damage over time. Examples of disorders associated with chronic kidney disease include, but are not limited to, type 1 diabetes, type 2 diabetes, high blood pressure, glomerulonephritis, interstitial nephritis, polycystic kidney disease, prolonged obstruction of the urinary tract (e.g., from conditions such as enlarged prostate, kidney stones and some cancers), vesicoureteral reflux, and recurrent kidney infection. Chronic kidney disease and its stages (CKD 1-5) can usually be characterized or classified accordingly, such as based on the presence of either kidney damage (albuminuria) or impaired estimated glomerular filtration rate (GFR<60 [ml/min/1.73 m$^2$], with or without kidney damage).

The term "level" or "amount" of a biomarker, as used herein, refers to the measurable quantity of a biomarker, e.g., an miRNA. The amount may be either (a) an absolute amount as measured in molecules, moles or weight per unit volume or cells or (b) a relative amount, e.g., measured by densitometric analysis.

As used herein, the term "known standard level", "reference level" or "control level" refers to an accepted or pre-determined level of the biomarker which is used to compare the biomarker level derived from the sample of a patient. In one embodiment, when compared to the known standard level of a certain biomarker, deviation from the known standard level generally indicates either an improvement or deterioration in the disease state. In one embodiment, when compared to the known standard level of a certain biomarker, deviation from the known standard level generally indicates an increased or decreased likelihood of disease progression in a subject. Alternatively, when compared to the known standard level of a certain biomarker, equivalence to the known standard level generally indicates confirmation of the disease activity, confirmation of a non-disease state, or, if the biomarker level of the patient is obtained following therapeutic treatment for the disease, failure of a therapy to improve a patient's disease state. In one embodiment, the known standard level of an miRNA is a level of the miRNA in a normoalbuminuric subject.

As used herein, the term "comparable level" refers to a level of one biomarker that is substantially similar to the level of another, e.g., a control level. In one embodiment, two biomarkers have a comparable level if the level of the biomarker is within one standard deviation of the control biomarker level. In another embodiment, two biomarkers have a comparable level if the level of the biomarker is 20% or less of the level of the control biomarker level.

As used herein, the term "ESRD progressor", "progressor" or "rapid progressor" refers to a subject having a disorder associated with chronic kidney disease who has been identified as having an elevated risk for developing ESRD. While an ESRD progressor has a disorder associated with chronic kidney disease, which may put the subject at risk for developing ESRD, the term is meant to include those subjects who have an identified risk elevated above that normally associated with the disorder associated with chronic kidney disease. In one embodiment, a progressor has a level of let-7b-5p and/or miR-21-5p that is statistically significantly higher than a non-progressor control level or a normoalbuminuric control, and, as such, has an increased risk for developing ESRD.

As used herein, the term "progressor miRNA" refers to an miRNA that is associated with increased risk of developing ESRD in a subject having a disorder associated with chronic kidney disease. Examples of progressor miRNAs include, but are not limited to, let-7b-5p and/or miR-21-5p. In one embodiment, an increase in the level of a progressor miRNA in a subject relative to a non-progressor level or a normoalbuminuric control indicates an increased risk that the subject will develop ESRD. In one embodiment, a progressor miRNA is an miRNA that is associated with increased risk of developing ESRD in a subject having a disorder associated with chronic kidney disease, wherein the miRNA is not let-7b-5p or miR-21-5p.

As used herein, the term "non-progressor" refers to a subject having a disorder associated with chronic kidney disease who has a reduced risk of developing ESRD. A non-progressor may be characterized as a subject having protective levels of let-7c-5p and/or miR-29a-3p. In one embodiment, a non-progressor is a subject having a disorder associated with chronic kidney disease who is in stage 1 or 2 CKD (Chronic Kidney Disease) but who has a lower risk of progressing to ESRD due, at least in part, to elevated or comparable levels of a protective miRNA (e.g., in comparison to a normoalbuminuric control). In one embodiment, a non-progressor is defined as a subject who has a level of let-7c-5p and/or miR-29a-3p that is statistically significantly higher than a progressor control level or is comparable to a normoalbuminuric control.

As used herein, the term "protective miRNA" refers to an miRNA that may be used to treat ESRD or is associated with a reduced chance that a subject having a disorder associated with chronic kidney disease will developing ESRD. When a protective miRNA is expressed at certain levels in the subject, then the subject has a reduced ESRD risk In one embodiment, an increase in the level of a protective miRNA relative to a progressor level confers a therapeutic benefit. In one embodiment, a comparable level of a protective miRNA relative to a normoalbuminuric control level confers a therapeutic benefit. Examples of protective miRNAs include, but are not limited to, let-7c-5p and miR-29a-3p. In one embodiment, the term protective miRNA refers to an miRNA that is associated with a decreased risk of developing ESRD in a subject having a disorder associated with chronic kidney disease, wherein the miRNA is not let-7c-5p and miR-29a-3p.

As used herein, the term "miRNA agent" refers an miRNA, or an agent (e.g., an oligonucleotide agent) that mimics, replicates, or stimulates the activity of the specific miRNA as a translational repressor of one or more of the specific miRNA's targets. An miRNA agent can include, for example, an miRNA mimic, a synthetic miRNA oligonucleotide, or an expression vector encoding the miRNA. In one embodiment, the miRNA agent is a "let-7c-5p agent". The term "let-7c-5p agent" refers to let-7c-5p, or an agent that mimics, replicates, or stimulates the activity of let-7c-5p as a translational repressor of one or more targets of let-7c-5p.

A let-7c-5p agent can include, for example, let-7c-5p (SEQ ID NO:16 as shown in Table 8; human), a let-7c-5p mimic, a synthetic let-7c-5p oligonucleotide, or an expression vector encoding let-7c-5p. In one embodiment, the miRNA agent is a "protective miRNA agent", which refers to an miRNA agent that is useful for treating or preventing ESRD, i.e. it provides a protective effect against development of ESRD. In certain embodiments, the protective miRNA agent is a let-7c-5p agent and/or an miR-29a-3p agent.

The term "therapeutically effective amount" refers to an amount which, when administered to a living subject, achieves a desired effect on the living subject. The exact amount will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. For example, an effective amount of an agent described herein for administration to the living subject is an amount that prevents and/or treats ESRD. For example, for a renal protective agent, a therapeutically effective amount can be an amount that has been shown to provide an observable therapeutic benefit compared to baseline clinically observable signs and symptoms of chronic kidney disease.

As used herein, the term "renal protective agent" refers to an agent that can prevent or delay the progression of nephropathy in a subject having moderately increased albuminuria or diabetic nephropathy. Examples of renal protective agents include, but are not limited to, angiotensin-converting enzyme (ACE) inhibitors and angiotensin-II receptor blockers (ARBs).

2. miRNAs for Determining Risk of ESRD Progression

The invention is based, at least in part, on the discovery that certain miRNAs are associated with progression to or protection from ESRD in subjects having a disorder associated with chronic kidney disease, such as diabetes. As described in the Examples below, the studies herein identified a class of progressor miRNAs whose levels can be used to predict whether a subject (having a disorder associated with chronic kidney disease, such as diabetes) will develop ESRD. Progressor miRNAs were identified in diabetic patients who showed symptoms of chronic kidney disease and were found to develop ESRD or reach CKD stage 4 within 3-11 years. In contrast, other patients (identified as non-progressors) showed initial kidney disease (e.g., CKD stage 1 or 2) but maintained their state of kidney disease over 7-20 years and did not progress to ESRD. Certain miRNAs with differential expression between the two groups (or with control normoalbuminuric) were identified as predictors (or protectors) of whether a subject having diabetes and chronic kidney disease would progress to ESRD.

As further described in the Examples, it has been shown herein that certain miRNAs are expressed at higher levels (e.g., at least 1.5 fold higher level) in progressors who are at risk for developing ESRD relative to either normoalbuminuric controls or to patients who are identified as not progressing to ESRD. Thus, in one embodiment, the invention relates to progressor miRNA biomarkers found to be differentially present in biological samples derived from subjects with diabetes having an increased risk of progression to ESRD, as compared with subjects who are identified as non-progressors (i.e. subjects with diabetes who do not progress to ESRD), or normoalbuminuric controls. These progressor miRNAs may be used to determine whether a subject having a disorder associated with chronic kidney disease, such as diabetes, has an increased risk for developing ESRD. In certain embodiments, the progressor miRNA is let-7b-5p and/or miR-21-5p. The invention also provides a class of protective miRNAs that are expressed at comparable levels to normoalbuminuric controls or at greater levels than progressor controls and decrease the likelihood a subject having a disorder associated with chronic kidney disease will progress to ESRD. These miRNAs impart protection such that the subject has a decreased risk for developing ESRD. These miRNAs also serve as the basis for therapeutic methods which provide ESRD protection to a subject in need thereof.

In one embodiment, a subject having diabetes who is at risk of developing ESRD may be identified by determining the relative level of a progressor miRNA in a sample from the subject, wherein a higher level of the progressor miRNA in the sample relative to a non-progressor control level of the progressor miRNA or a normoalbuminuric control level of the progressor miRNA indicates that the subject is at risk of developing ESRD.

Determining whether a level of an miRNA in a biological sample derived from a test subject is different from the level of the miRNA present in a control subject may be ascertained by comparing the level of the miRNA in the sample from the test subject with a suitable control, e.g., a normoalbuminuric control, a progressor control, or a non-progressor control, of the same miRNA. The skilled person can select an appropriate control for the assay in question. For example, a suitable control may be a biological sample derived from a known subject, e.g., a non-progressor or a normoalbuminuric control.

In one embodiment, in determining whether a subject is a progressor and has elevated levels of miRNA associated with progression to ESRD, a statistically significant increase in the level of an miRNA in a sample from the subject relative to the suitable control is indicative that the subject is at risk of developing ESRD. Alternatively, if a suitable control is obtained from a subject known to have ESRD (a rapid progressor), levels comparable to such a control are indicative of a risk of developing ESRD.

In one embodiment, in determining whether a subject is a non-progressor and has levels of miRNA associated with protection from ESRD, a comparable level of an miRNA in a sample from the subject relative to the suitable control, e.g., a non-progressor or a normoalbuminuric control, is indicative that the subject has a reduced risk of developing ESRD. Alternatively, if a suitable control is obtained from a subject known to have ESRD (a rapid progressor), levels of protective miRNA that are higher relative to such a control are indicative of a reduced risk of developing ESRD.

Generally, a suitable control may also be a reference standard. A reference standard serves as a reference level for comparison, such that test samples can be compared to the reference standard in order to infer the ESRD status of a subject. A reference standard may be representative of the level of one or more miRNA biomarkers in a known subject, e.g., a subject known to be a normal subject (healthy without chronic kidney disease), or a subject known to have ESRD. Likewise, a reference standard may be representative of the level of one or more miRNAs in a population of known subjects, e.g., a population of subjects known to be normal subjects, or a population of subjects known to have ESRD or a risk of developing ESRD. The reference standard may be obtained, for example, by pooling samples from a plurality of individuals and determining the level of an miRNA biomarker in the pooled samples, to thereby produce a standard over an averaged population. Such a reference standard represents an average level of an miRNA among a population of individuals. A reference standard may also be obtained, for example, by averaging the level of an miRNA determined to be present in individual samples obtained from a plurality of individuals. Such a standard is also representative of an average level of an miRNA among a population of individuals. A reference standard may also be a collection of values each representing the level of an miRNA in a known subject in a population of individuals. In certain embodiments, test samples may be compared against such a collection of values in order to infer the risk status of a subject. In certain embodiments, the reference standard is an absolute value. In such embodiments, test samples may be compared against the absolute value in order to infer the risk status of a subject. In one embodiment, a comparison between the level of one or more miRNAs in a sample relative to a suitable control is made by executing a software classification algorithm. The skilled person can readily envision additional suitable controls that may be appropriate depending on the assay in question. The aforementioned suitable controls are exemplary, and are not intended to be limiting.

In certain aspects, the present invention features a method for identifying a subject who is at risk of developing ESRD, said method comprising determining the relative level of a progressor miRNA in a sample from the subject, wherein a higher level of the progressor miRNA in the sample relative to a non-progressor control level of the progressor miRNA or a normoalbuminuric control level of the progressor miRNA indicates that the subject is at risk of developing ESRD. In other aspects, the present invention features a method for identifying a subject who has a reduced risk for developing ESRD, the method comprising determining the relative level of a protective miRNA in a sample from the subject, wherein a higher level of the protective miRNA in the sample relative to a progressor control level of the protective miRNA or a comparable level of the protective miRNA to a normoalbuminuric control level of the protective miRNA indicates that the subject is not at risk of developing ESRD.

In one embodiment, the method comprises determining the relative level of the progressor miRNA in a sample from the subject, and determining the relative level of the protective miRNA in a sample from the subject. In certain embodiments, the progressor miRNA is let-7b-5p and/or miR-21-5p. In other embodiments, the protective miRNA is let-7c-5p and/or miR-29a-3p.

Generally, an increase in the level of let-7b-5p and miR-21-5p in a biological sample from a test subject relative the level of let-7b-5p and miR-21-5p in a biological sample from a control (e.g., a nonprogressor), indicates that the subject is at increased risk of developing ESRD.

Generally, a decrease in the level of let-7c-5p and miR-29a-3p in a biological sample from a test subject relative the level of let-7c-5p and miR-29a-3p in a biological sample from a control (e.g., a non-progressor), indicates that the subject is at increased risk of developing ESRD.

Other miRNAs that may be used to determine risk of ESRD and/or protection from ESRD include miR-10b-5p, miR-451a, miR-199a-5p, miR-3907, miR-143-3p, miR-19b-3p, miR-22-5p, miR-221-3p, miR-24-3p, miR-4507, miR-4539, miR-631, miR-766-3p, miR-3940-5p, miR-3200-5p, miR-1537-3p, miR-4505, miR-93-3p, miR-15b-3p, miR-663a, miR-1909-5p, miR-4446-3p and miR-373-5p.

Table 8 provides a list of miRNAs identified and useful in the methods of the present invention, miR base accession number and nucleic acid sequence. Included in Table 8 are the following miRNAs: miR-10b-5p, miR-451a, miR-199a-5p, miR-3907, miR-143-3p, miR-19b-3p, miR-22-5p, miR-221-3p, miR-24-3p, miR-4507, miR-4539, miR-631, miR-766-3p, miR-394.0-5p, miR-3200-5p, let-7c-5p, miR-29a-3p, miR-1537-3p, miR-4505, miR-93-3p, miR-15b-3p, miR-663a, let-7b-5p, miR-21-5p, miR-1909-5p, miR-4446-3p and miR-373-5p.

The miRNAs described herein can be used individually or in combination in methods to identify (e.g. diagnostic tests) a risk of developing ESRD in a subject. The methods also include monitoring the course of progression to ESRD. Based on the risk of progression to ESRD in a subject, additional procedures may be indicated, including, for example, additional diagnostic tests or therapeutic procedures.

Common tests for statistical significance also include, but are not limited to, t-test, ANOVA, Kniskal-Wallis, Wilcoxon, Mann-Whitney, and odds ratio. miRNA biomarkers, alone or in combination, can be used to provide a measure of the relative risk that a subject is or is not at risk for progression to ESRD.

The present invention has identified particular biomarkers that are differentially present in subjects who are at risk of developing ESRD relative to non-progressors. The biomarkers listed in Table 8 are differentially present in biological samples derived from subjects who are rapid progressors or non-progressors, and thus each is individually useful in facilitating the determination of a risk of developing ESRD in a test subject. Such a method involves determining the level of the biomarker in a sample derived from the subject. Determining the level of the biomarker in a sample may include measuring, detecting, or assaying the level of the biomarker in the sample using any suitable method, for example, the methods set forth herein. Determining the level of the biomarker in a sample may also include examining the results of an assay that measured, detected, or assayed the level of the biomarker in the sample. The method may also involve comparing the level of the biomarker in a sample with a suitable control. A change in the level of the biomarker relative to that in a normal subject as assessed using a suitable control is indicative of the risk of progression to ESRD of the subject. A diagnostic amount of a biomarker that represents an amount of the biomarker above or below which a subject is classified as having a particular risk status can be used. For example, if the biomarker is downregulated in samples derived from the subject sample as compared to a control sample, a measured amount below the diagnostic cutoff provides an indication of risk of developing ESRD. Alternatively, if the biomarker is upregulated in samples derived from the subject sample as compared to a control sample, a measured amount above the diagnostic cutoff provides an indication of risk of developing ESRD. Generally, let-7b-5p and miR-21-5p are up-regulated in rapid progressors relative to non-progressors or normoalbuminuric controls. Generally, let-7c-5p and miR-29a-3p are down-regulated in rapid progressors relative to non-progressors or normoalbuminuric controls.

As is well-understood in the art, adjusting the particular diagnostic cut-off used in an assay allows one to adjust the sensitivity and/or specificity of the diagnostic assay as desired. The particular diagnostic cut-off can be determined, for example, by measuring the amount of the biomarker in a statistically significant number of samples from subjects with different risk statuses, and drawing the cut-off at the desired level of accuracy, sensitivity, and/or specificity. In certain embodiments, the diagnostic cut-off can be determined with the assistance of a classification algorithm, as described herein.

Optionally, the method may further comprise providing a diagnosis that the subject is or is not at risk of developing ESRD based on the level of at least one miRNA in the sample. In addition or alternatively, the method may further comprise correlating a difference in the level or levels of at least one miRNA relative to a suitable control with a diagnosis of ESRD.

While individual miRNA biomarkers are useful in identifying a subject who is at risk of developing ESRD, as shown herein, a combination of miRNA biomarkers may also be used to provide a greater predictive value of risk of developing ESRD. Specifically, the detection of a plurality of miRNA biomarkers can increase the accuracy, sensitivity, and/or specificity of a diagnostic test. Accordingly, the present invention includes the individual biomarkers described herein, and also biomarker combinations, and their use in methods and kits described herein. In certain embodiments, the levels of at least two miRNAs in the sample are determined, wherein the miRNAs are selected from miR-10b-5p, miR-451a, miR-199a-5p, miR-3907, miR-143-3p, miR-19b-3p, miR-22-5p, miR-221-3p, miR-24-3p, miR-4507, miR-4539, miR-631, miR-766-3p, miR-3940-5p, miR-3200-5p, let-7c-5p, miR-29a-3p, miR-1537-3p, miR-4505, miR-93-3p, miR-15b-3p, miR-663a, let-7b-5p, miR-21-5p, miR-1909-5p, miR-4446-3p and miR-373-5p. The level of miRNAs indicative of the risk of development of ESRD may be used as a stand-alone diagnostic indicator of risk in a subject. Optionally, the methods may include the performance of at least one additional test to facilitate identifying a subject who is at risk of developing ESRD. For example, ESRD may be diagnosed using the Glomerular Filtration Rate (GFR) test, where a CKD at stage 5 (kidney failure) is determined by a GFR of less than 15. Alternatively, ESRD can be determined by measuring albuminuria in the blood of a subject, wherein an albuminuria level of A3 may indicate progression to ESRD.

In one embodiment, the invention features a method of diagnosing end-stage renal disease (ESRD) in a patient, said method comprising obtaining a plasma sample from a human patient, detecting the relative level of let-7b-5p in the sample by quantitative PCR (qPCR), hybridization analysis, or microarray analysis to detect let-7b-5p, and diagnosing the patient with ESRD when a higher level of let-7b-5p in comparison to either a non-progressor control level of let-7b-5p or a normoalbuminuric control level of let-7b-5p in the plasma sample is detected.

In one embodiment, the invention features a method of identifying a subject who is at risk of developing ESRD, said method comprising obtaining a plasma sample from a human patient, detecting the relative level of let-7b-5p in the sample by quantitative PCR (qPCR), hybridization analysis, or microarray analysis to detect let-7b-5p, and identifying the subject who is at risk of developing ESRD when a higher level of let-7b-5p in comparison to either a non-progressor control level of let-7b-5p or a normoalbuminuric control level of let-7b-5p in the plasma sample is detected.

In one embodiment, the invention features a method of diagnosing end-stage renal disease (ESRD) in a patient, said method comprising obtaining a plasma sample from a human patient, detecting the relative level of miR-21-5p in the sample by quantitative PCR (qPCR), hybridization analysis, or microarray analysis to detect miR-21-5p, and diagnosing the patient with ESRD when a higher level of miR-21-5p in comparison to either a non-progressor control level of miR-21-5p or a normoalbuminuric control level of miR-21-5p in the plasma sample is detected.

In one embodiment, the invention features a method of identifying a subject who is at risk of developing ESRD, said method comprising obtaining a plasma sample from a human patient, detecting the relative level of miR-21-5p in the sample by quantitative PCR (qPCR), hybridization analysis, or microarray analysis to detect miR-21-5p, and identifying the subject who is at risk of developing ESRD when a higher level of miR-21-5p in comparison to either a non-progressor control level of miR-21-5p or a normoalbuminuric control level of miR-21-5p in the plasma sample is detected.

In one embodiment, the invention features a method of identifying a subject who is a non-progressor, said method comprising obtaining a plasma sample from a human patient, detecting the relative level of let-7c-5p in the plasma sample by quantitative PCR (qPCR), hybridization analysis, or microarray analysis to detect let-7c-5p, and identifying a subject who is a non-progressor when a comparable level of let-7c-5p relative to a normoalbuminuric control level of let-7c-5p or a higher level of let-7c-5p relative to a non-progressor control level of let-7c-5p is detected. In one embodiment, the patient has a disorder associated with chronic kidney disease.

In one embodiment, the invention features a method of identifying a subject who is a non-progressor, said method comprising obtaining a plasma sample from a human patient, detecting the relative level of miR-29a-3p in the plasma sample by quantitative PCR (qPCR), hybridization analysis, or microarray analysis to detect miR-29a-3p, and identifying a subject who is a non-progressor when a comparable level of miR-29a-3p relative to a normoalbuminuric control level of miR-29a-3p or a higher level of miR-29a-3p relative to a non-progressor control level of miR-29a-3p is detected. In one embodiment, the patient has a disorder associated with chronic kidney disease.

3. Biological Samples

The expression level of one or more miRNAs may be determined in a biological sample derived from a subject. A sample derived from a subject is one that originates and is obtained from a subject. Such a sample may be further processed after it is obtained from the subject. For example, RNA may be isolated from a sample. In this example, the RNA isolated from the sample is also a sample derived from a subject. A biological sample useful for determining the level of one or more miRNAs may be obtained from essentially any source, as miRNA expression has been reported in cells, tissues, and fluids throughout the body. However, in one aspect of the invention, levels of one or more miRNAs indicative of a risk in a subject having diabetes of developing ESRD may be detected in a sample obtained from a subject non-invasively.

In a preferred embodiment, the biological sample used for determining the level of one or more miRNAs is a sample containing circulating miRNAs, e.g., extracellular miRNAs. Extracellular miRNAs freely circulate in a wide range of biological material, including bodily fluids, such as fluids from the circulatory system, e.g., a blood sample or a lymph sample, or from another bodily fluid such as CSF, urine or saliva. Accordingly, in some embodiments, the biological sample used for determining the level of one or more miRNA biomarkers is a bodily fluid, for example, blood, fractions thereof, serum, plasma, urine, saliva, tears, sweat, semen, vaginal secretions, lymph, bronchial secretions, CSF, etc. In some embodiments, the sample is a sample that is obtained non-invasively. In one embodiment, the sample is a plasma sample.

Circulating miRNAs include miRNAs in cells (cellular miRNA), extracellular miRNAs in microvesicles (microvesicle-associated miRNA), and extracellular miRNAs that are not associated with cells or microvesicles (extracellular, non-vesicular miRNA). In some embodiments, the biological sample used for determining the level of one or more miRNA biomarkers (e.g., a sample containing circulating miRNA) may contain cells. In other embodiments, the biological sample may be free or substantially free of cells (e.g., a serum sample). The sample may likewise be free or substantially free of microvesicles. For example, a sample that is free or substantially free of microvesicles is one in which the microvesicle content of the sample is sufficiently low to avoid interfering with the ability to accurately determine the level of non-vesicular miRNAs in the sample. In some embodiments, a sample containing circulating miRNAs, e.g., extracellular miRNAs, is a blood-derived sample. Exemplary blood-derived sample types include, e.g., a plasma sample, a serum sample, a blood sample, etc. In other embodiments, a sample containing circulating miRNAs is a lymph sample. Circulating miRNAs are also found in urine and saliva, and biological samples derived from these sources are likewise suitable for determining the level of one or more miRNAs.

4. Determining the Level of miRNAs in a Sample

As described above, miRNAs indicative of a risk of progression to ESRD were discovered. Progressor and protective miRNAs were identified by comparing the level of expression of miRNAs in normoalbuminuric control samples, in baseline plasma specimens from subjects with diabetes who were at risk for rapid progression to ESRD (rapid progressors), and from subjects with diabetes who were determined to have stable renal function (nonprogressors). A number of differentially present miRNAs were identified in this manner, and were determined to be indicative of a risk of progression to ESRD. Specifically, the relative levels of let-7b-5p, let-7c-5p, miR-21-5p, and miR-29a-3p were found to be significantly different in baseline specimens from patients with proteinuria who subsequently lost renal function (i.e., rapid progressors), those who maintained normal and stable renal function over the follow-up period (i.e., nonprogressors), and normoalbuminuric control subjects.

The miRNAs identified herein can be used to determine the risk of progression to ESRD of a subject, for example, a subject who has diabetes (e.g., type 1 diabetes), and whose risk of progression to ESRD was previously unknown. This may be accomplished by determining the level of one or more of let-7b-5p, let-7c-5p, miR-21-5p, and miR-29a-3p, or combinations thereof, in a biological sample derived from the subject. A difference in the level of one or more of these miRNA biomarkers as compared to that in a biological sample derived from a normal subject may be predictive regarding whether the subject has a risk of developing ESRD.

The level of one or more miRNA biomarkers in a biological sample may be determined by any suitable method. Any reliable method for measuring the level or amount of miRNA in a sample may be used. Generally, miRNA can be detected and quantified from a sample (including fractions thereof), such as samples of isolated RNA by various methods known for mRNA, including, for example, amplification-based methods (e.g., Polymerase Chain Reaction (PCR), Real-Time Polymerase Chain Reaction (RT-PCR), Quantitative Polymerase Chain Reaction (qPCR), rolling circle amplification, etc.), hybridization-based methods (e.g., hybridization arrays (e.g., microarrays), NanoString analysis, Northern Blot analysis, branched DNA (bDNA) signal amplification, in situ hybridization, etc.), and sequencing-based methods (e.g., next-generation sequencing methods, for example, using the Illumina or IonTorrent platforms). Other exemplary techniques include ribonuclease protection assay (RPA) and mass spectroscopy. In one embodiment, the level of the miRNA in a sample is determined using quantitative PCR (qPCR) or a Northern blot.

In some embodiments, RNA is converted to DNA (cDNA) prior to analysis. cDNA can be generated by reverse transcription of isolated miRNA using conventional techniques. miRNA reverse transcription kits are known and commercially available. Examples of suitable kits include, but are not limited to the MIRVANA TaqMan. miRNA transcription kit (Ambion, Austin, Tex.), and the TaqMan. miRNA transcription kit (Applied Biosystems, Foster City, Calif.). Universal primers, or specific primers, including miRNA-specific stem-loop primers, are known and commercially available, for example, from Applied Biosystems. In some embodiments, miRNA is amplified prior to measurement. In other embodiments, the level of miRNA is measured during the amplification process. In still other embodiments, the level of miRNA is not amplified prior to measurement. Some exemplary methods suitable for determining the level of miRNA in a sample are described in greater detail below. These methods are provided by way of illustration only, and it will be apparent to a skilled person that other suitable methods may likewise be used.

A. Amplification-Based Methods

Many amplification-based methods exist for detecting the level of miRNA nucleic acid sequences, including, but not limited to, PCR, RT-PCR, qPCR, and rolling circle amplification. Other amplification-based techniques include, for example, ligase chain reaction, multiplex ligatable probe amplification, in vitro transcription (IVT), strand displacement amplification, transcription-mediated amplification, RNA (Eberwine) amplification, and other methods that are known to persons skilled in the art.

A typical PCR reaction includes multiple steps, or cycles, that selectively amplify target nucleic acid species: a denaturing step, in which a target nucleic acid is denatured; an annealing step, in which a set of PCR primers (i.e., forward and reverse primers) anneal to complementary DNA strands, and an elongation step, in which a thermostable DNA polymerase elongates the primers. By repeating these steps multiple times, a DNA fragment is amplified to produce an amplicon, corresponding to the target sequence. Typical PCR reactions include 20 or more cycles of denaturation, annealing, and elongation. In many cases, the annealing and elongation steps can be performed concurrently, in which case the cycle contains only two steps. A reverse transcription reaction (which produces a cDNA sequence having complementarity to a miRNA) may be performed prior to PCR amplification. Reverse transcription reactions include the use of, e.g., a RNA-based DNA polymerase (reverse transcriptase) and a primer.

Kits for quantitative real time PCR of miRNA are known, and are commercially available. Examples of suitable kits include, but are not limited to, the TaqMan. miRNA Assay (Applied Biosystems) and the MIRVANA qRT-PCR miRNA detection kit (Ambion). The miRNA can be ligated to a single stranded oligonucleotide containing universal primer sequences, a polyadenylated sequence, or adaptor sequence prior to reverse transcriptase and amplified using a primer complementary to the universal primer sequence, poly(T) primer, or primer comprising a sequence that is complementary to the adaptor sequence.

In some instances, custom qRT-PCR assays can be developed for determination of miRNA levels. Custom qRT-PCR assays to measure miRNAs in a biological sample, e.g., a body fluid, can be developed using, for example, methods that involve an extended reverse transcription primer and locked nucleic acid modified PCR. Custom miRNA assays can be tested by running the assay on a dilution series of chemically synthesized miRNA corresponding to the target sequence. This permits determination of the limit of detection and linear range of quantitation of each assay. Furthermore, when used as a standard curve, these data permit an estimate of the absolute abundance of miRNAs measured in biological samples.

Amplification curves may optionally be checked to verify that Ct values are assessed in the linear range of each amplification plot. Typically, the linear range spans several orders of magnitude. For each candidate miRNA assayed, a chemically synthesized version of the miRNA can be obtained and analyzed in a dilution series to determine the limit of sensitivity of the assay, and the linear range of quantitation. Relative expression levels may be determined, for example, according to the 2(-ΔΔC(T)) Method, as described by Livak et al., Analysis of relative gene expression data using real-time quantitative PCR and the 2(-ΔΔC (T)) Method. Methods (2001) December; 25(4):402-8.

In some embodiments, two or more miRNAs are amplified in a single reaction volume. For example, multiplex q-PCR, such as qRT-PCR, enables simultaneous amplification and quantification of at least two miRNAs of interest in one reaction volume by using more than one pair of primers and/or more than one probe. The primer pairs comprise at least one amplification primer that specifically binds each miRNA, and the probes are labeled such that they are distinguishable from one another, thus allowing simultaneous quantification of multiple miRNAs.

Rolling circle amplification is a DNA-polymerase driven reaction that can replicate circularized oligonucleotide probes with either linear or geometric kinetics under isothermal conditions (see, for example, Lizardi et al., Nat. Gen. (1998) 19(3):225-232; Gusev et al., Am. J. Pathol. (2001) 159(1):63-69; Nallur et al., Nucleic Acids Res. (2001) 29(23):E118). In the presence of two primers, one hybridizing to the (+) strand of DNA, and the other hybridizing to the (-) strand, a complex pattern of strand displacement results in the generation of over 10 9 copies of each DNA molecule in 90 minutes or less. Tandemly linked copies of a closed circle DNA molecule may be formed by using a single primer. The process can also be performed using a matrix-associated DNA. The template used for rolling circle amplification may be reverse transcribed. This method can be used as a highly sensitive indicator of miRNA sequence and expression level at very low miRNA concentrations (see, for example, Cheng et al., Angew Chem. Int. Ed. Engl. (2009) 48(18):3268-72; Neubacher et al., Chembiochem. (2009) 10(8):1289-91).

B. Hybridization-Based Methods miRNA may be detected using hybridization-based methods, including but not limited to hybridization arrays (e.g., microarrays), NanoString analysis, Northern Blot analysis, branched DNA (bDNA) signal amplification, and in situ hybridization.

Microarrays can be used to measure the expression levels of large numbers of miRNAs simultaneously. Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays. Also useful are microfluidic TaqMan Low-Density Arrays, which are based on an array of microfluidic qRT-PCR reactions, as well as related microfluidic qRT-PCR based methods.

In one example of microarray detection, various oligonucleotides (e.g., 200+5'-amino-modified-C6 oligos) corresponding to human sense miRNA sequences are spotted on three-dimensional CodeLink slides (GE Health/Amersham Biosciences) at a final concentration of about 20 µM and processed according to manufacturer's recommendations. First strand cDNA synthesized from 20 µg TRIzol-purified total RNA is labeled with biotinylated ddUTP using the Enzo BioArray end labeling kit (Enzo Life Sciences Inc.). Hybridization, staining, and washing can be performed according to a modified Affymetrix Antisense genome array protocol.

Axon B-4000 scanner and Gene-Pix Pro 4.0 software or other suitable software can be used to scan images. Non-positive spots after background subtraction, and outliers detected by the ESD procedure, are removed. The resulting signal intensity values are normalized to per-chip median values and then used to obtain geometric means and standard errors for each miRNA. Each miRNA signal can be transformed to log base 2, and a one-sample t test can be conducted. Independent hybridizations for each sample can be performed on chips with each miRNA spotted multiple times to increase the robustness of the data.

Microarrays can be used for the expression profiling of miRNAs in diseases. For example, RNA can be extracted from a sample and, optionally, the miRNAs are size-selected from total RNA. Oligonucleotide linkers can be attached to the 5' and 3' ends of the miRNAs and the resulting ligation products are used as templates for an RT-PCR reaction. The sense strand PCR primer can have a fluorophore attached to its 5' end, thereby labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the, capture probes are affixed. The spot will then fluoresce when excited using a microarray laser scanner.

The fluorescence intensity of each spot is then evaluated in terms of the number of copies of a particular miRNA, using a number of positive and negative controls and array data normalization methods, which will result in assessment of the level of expression of a particular miRNA.

Total RNA containing the miRNA extracted from a body fluid sample can also be used directly without size-selection of the miRNAs. For example, the RNA can be 3' end labeled using T4 RNA ligase and a fluorophore-labeled short RNA linker. Fluorophore-labeled miRNAs complementary to the corresponding miRNA capture probe sequences on the array hybridize, via base pairing, to the spot at which the capture probes are affixed. The fluorescence intensity of each spot is then evaluated in terms of the number of copies of a particular miRNA, using a number of positive and negative controls and array data normalization methods, which will result in assessment of the level of expression of a particular miRNA.

Several types of microarrays can be employed including, but not limited to, spotted oligonucleotide microarrays, pre-fabricated oligonucleotide microarrays or spotted long oligonucleotide arrays.

miRNAs can also be detected without amplification using the nCounter Analysis System (NanoString Technologies, Seattle, Wash.). This technology employs two nucleic acid-based probes that hybridize in solution (e.g., a reporter probe and a capture probe). After hybridization, excess probes are removed, and probe/target complexes are analyzed in accordance with the manufacturer's protocol. nCounter miRNA assay kits are available from NanoString Technologies, which are capable of distinguishing between highly similar miRNAs with great specificity. miRNAs can also be detected using branched DNA (bDNA) signal amplification (see, for example, Urdea, Nature Biotechnology (1994), 12:926-928). miRNA assays based on bDNA signal amplification are commercially available. One such assay is the QUANTIGENE 2.0 miRNA Assay (Affymetrix, Santa Clara, Calif.).

Northern Blot and in situ hybridization may also be used to detect miRNAs. Suitable methods for performing Northern Blot and in situ hybridization are known in the art.

C. Sequencing-Based Methods

Advanced sequencing methods can likewise be used as available. For example, miRNAs can be detected using ILLUMINA Next Generation Sequencing (e.g., Sequencing-By-Synthesis or TruSeq methods, using, for example, the HiSeq, HiScan, GenomeAnalyzer, or MiSeq systems (Illumina, Inc., San Diego, Calif.)).

Next-generation sequencing (NGS), also known as high-throughput sequencing, is the catch-all term used to describe a number of different modern sequencing technologies including Illumina (Solexa) sequencing, Roche 454 sequencing, SOLiD sequencing and Ion torrent sequencing. In Illumina sequencing, 100-150 bp reads are used. Somewhat longer fragments are ligated to generic adaptors and annealed to a slide using the adaptors. PCR is carried out to amplify each read, creating a spot with many copies of the same read. They are then separated into single strands to be sequenced. Roche 454 sequencing can sequence much longer reads than Illumina. Like Illumina, it does this by sequencing multiple reads at once by reading optical signals as bases are added. Applied Biosystems SOLiD system, is a next-generation sequencing platform that can to perform massivley parallel sequencing of clonally-amplified DNA fragments. The SOLiD sequencing method is based on sequencing by ligation of dye-labeled oligonucleotides. miRNAs can also be detected using Ion Torrent Sequencing (Ion Torrent Systems, Inc., Gulliford, Conn.), or other suitable methods of semiconductor sequencing. Ion semiconductor sequencing is a method of DNA sequencing based on the detection of hydrogen ions that are released during the polymerization of DNA. This is a method of "sequencing by synthesis", during which a complementary strand is built based on the sequence of a template strand. A microwell containing a template DNA strand to be sequenced is flooded with a single species of deoxyribonucleotide triphosphate (dNTP). If the introduced dNTP is complementary to the leading template nucleotide, it is incorporated into the growing complementary strand. This causes the release of a hydrogen ion that triggers an ISFET ion sensor, which indicates that a reaction has occurred. If homopolymer repeats are present in the template sequence, multiple dNTP molecules will be incorporated in a single cycle. This leads to a corresponding number of released hydrogens and a proportionally higher electronic signal.

D. Additional miRNA Detection Tools

Mass spectroscopy can be used to quantify miRNA using RNase mapping. Isolated RNAs can be enzymatically digested with RNA endonucleases (RNases) having high specificity (e.g., RNase Tl, which cleaves at the 3'-side of all unmodified guanosine residues) prior to their analysis by MS or tandem MS (MS/MS) approaches. The first approach developed utilized the on-line chromatographic separation of endonuclease digests by reversed phase HPLC coupled directly to ESI-MS. The presence of posttranscriptional modifications can be revealed by mass shifts from those expected based upon the RNA sequence. Ions of anomalous mass/charge values can then be isolated for tandem MS sequencing to locate the sequence placement of the post-transcriptionally modified nucleoside.

Matrix-assisted laser desorption/ionization mass spectrometry (MALDI-MS) has also been used as an analytical approach for obtaining information about posttranscriptionally modified nucleosides. MALDI-based approaches can be differentiated from ESI-based approaches by the separation step. In MALDI-MS, the mass spectrometer is used to separate the miRNA.

To analyze a limited quantity of intact miRNAs, a system of capillary LC coupled with nanoESl-MS can be employed, by using a linear ion trap-orbitrap hybrid mass spectrometer (LTQ Orbitrap XL, Thermo Fisher Scientific) or a tandem-quadrupole time-of-flight mass spectrometer (QSTAR® XL, Applied Biosystems) equipped with a custom-made nanospray ion source, a Nanovolume Valve (Valco Instruments), and a splitless nano HPLC system (DiNa, KYA Technologies). Analyte/TEAA is loaded onto a nano-LC trap column, desalted, and then concentrated. Intact miRNAs are eluted from the trap column and directly injected into a Cl 8 capillary column, and chromatographed by RP-HPLC using a gradient of solvents of increasing polarity. The chromatographic eluent is sprayed from a sprayer tip attached to the capillary column, using an ionization voltage that allows ions to be scanned in the negative polarity mode.

Additional methods for miRNA detection and measurement include, for example, strand invasion assay (Third Wave Technologies, Inc.), surface plasmon resonance (SPR), cDNA, MTDNA (metallic DNA; Advance Technologies, Saskatoon, SK), and single-molecule methods such as the one developed by US Genomics. Multiple miRNAs can be detected in a microarray format using a novel approach that combines a surface enzyme reaction with nanoparticle-amplified SPR imaging (SPRI). The surface reaction of poly(A) polymerase creates poly(A) tails on miRNAs hybridized onto locked nucleic acid (LNA) microarrays. DNA-modified nanoparticles are then adsorbed onto the poly(A) tails and detected with SPRI. This ultrasensitive nanoparticle-amplified SPRI methodology can be used for miRNA profiling at attamole levels.

E. Detection of Amplified or Non-Amplified miRNAs

In certain embodiments, labels, dyes, or labeled probes and/or primers are used to detect amplified or unamplified miRNAs. The skilled artisan will recognize which detection methods are appropriate based on the sensitivity of the detection method and the abundance of the target. Depending on the sensitivity of the detection method and the abundance of the target, amplification may or may not be required prior to detection. One skilled in the art will recognize the detection methods where miRNA amplification is preferred.

A probe or primer may include standard (A, T or U, G and C) bases, or modified bases. Modified bases include, but are not limited to, the AEGIS bases (from Eragen Biosciences), which have been described, e.g., in U.S. Pat. Nos. 5,432,272, 5,965,364, and 6,001,983. In certain aspects, bases are joined by a natural phosphodiester bond or a different chemical linkage. Different chemical linkages include, but are not limited to, a peptide bond or a Locked Nucleic Acid (LNA) linkage, which is described, e.g., in U.S. Pat. No. 7,060,809.

In a further aspect, oligonucleotide probes or primers present in an amplification reaction are suitable for monitoring the amount of amplification product produced as a function of time. In certain aspects, probes having different single stranded versus double stranded character are used to detect the nucleic acid. Probes include, but are not limited to, the 5'-exonuclease assay (e.g., TaqMan) probes (see U.S. Pat. No. 5,538,848), stem-loop molecular beacons (see, e.g., U.S. Pat. Nos. 6,103,476 and 5,925,517), stemless or linear beacons (see, e.g., WO 9921881, U.S. Pat. Nos. 6,485,901 and 6,649,349), peptide nucleic acid (PNA) Molecular Beacons (see, e.g., U.S. Pat. Nos. 6,355,421 and 6,593,091), linear PNA beacons (see, e.g. U.S. Pat. No. 6,329,144), non-FRET probes (see, e.g., U.S. Pat. No. 6,150,097), SUNRISE/AMPLIFLUORB. probes (see, e.g., U.S. Pat. No. 6,548,250), stem-loop and duplex SCORPION probes (see, e.g., U.S. Pat. No. 6,589,743), bulge loop probes (see, e.g., U.S. Pat. No. 6,590,091), pseudo knot probes (see, e.g., U.S. Pat. No. 6,548,250), cyclicons (see, e.g., U.S. Pat. No. 6,383,752), MGB ECLIPSE probe (Epoch Biosciences), hairpin probes (see, e.g., U.S. Pat. No. 6,596,490), PNA light-up probes, antiprimer quench probes (Li et al., Clin. Chem. 53:624-633 (2006)), self-assembled nanoparticle probes, and ferrocene-modified probes described, for example, in U.S. Pat. No. 6,485,901.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels.

In some aspects, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv) provides a member of a binding complex or affinity set, e.g., affinity, antibody-antigen, ionic complexes, hapten-ligand (e.g., biotin-avidin). In still other aspects, use of labels can be accomplished using any one of a large number of known techniques employing known labels, linkages, linking groups, reagents, reaction conditions, and analysis and purification methods.

miRNAs can be detected by direct or indirect methods. In a direct detection method, one or more miRNAs are detected by a detectable label that is linked to a nucleic acid molecule. In such methods, the miRNAs may be labeled prior to binding to the probe. Therefore, binding is detected by screening for the labeled miRNA that is bound to the probe. The probe is optionally linked to a bead in the reaction volume.

In certain embodiments, nucleic acids are detected by direct binding with a labeled probe, and the probe is subsequently detected. In one embodiment of the invention, the nucleic acids, such as amplified miRNAs, are detected using FlexMAP Microspheres (Luminex) conjugated with probes to capture the desired nucleic acids. Some methods may involve detection with polynucleotide probes modified with fluorescent labels or branched DNA (bDNA) detection, for example.

In other embodiments, nucleic acids are detected by indirect detection methods. For example, a biotinylated probe may be combined with a streptavidin-conjugated dye to detect the bound nucleic acid. The streptavidin molecule binds a biotin label on amplified miRNA, and the bound miRNA is detected by detecting the dye molecule attached to the streptavidin molecule. In one embodiment, the streptavidin-conjugated dye molecule comprises PHYCOLINK Streptavidin R-Phycoerythrin (PROzyme). Other conjugated dye molecules are known to persons skilled in the art.

Labels include, but are not limited to: light-emitting, light-scattering, and light-absorbing compounds which generate or quench a detectable fluorescent, chemiluminescent, or bioluminescent signal (see, e.g., Kricka, L., Nonisotopic DNA Probe Techniques, Academic Press, San Diego (1992) and Garman A., Non-Radioactive Labeling, Academic Press (1997).). A dual labeled fluorescent probe that includes a reporter fluorophore and a quencher fluorophore is used in some embodiments. It will be appreciated that pairs of fluorophores are chosen that have distinct emission spectra so that they can be easily distinguished.

In certain embodiments, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups (see, e.g., Blackburn et al., eds. "DNA and RNA Structure" in Nucleic Acids in Chemistry and Biology (1996)).

In other embodiments, methods relying on hybridization and/or ligation to quantify miRNAs may be used, including oligonucleotide ligation (OLA) methods and methods that allow a distinguishable probe that hybridizes to the target nucleic acid sequence to be separated from an unbound probe. As an example, HARP-like probes, as disclosed in U.S. Publication No. 2006/0078894 may be used to measure the quantity of miRNAs. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding unhybridized HARP probe. The agent is able to inactivate or modify the unhybridized HARP probe such that it cannot be amplified.

A probe ligation reaction may also be used to quantify miRNAs. In a Multiplex Ligation-dependent Probe Amplification (MLPA) technique (Schouten et al., Nucleic Acids Research 30:e57 (2002)), pairs of probes which hybridize immediately adjacent to each other on the target nucleic acid are ligated to each other driven by the presence of the target nucleic acid. In some aspects, MLPA probes have flanking PCR primer binding sites. MLPA probes are specifically amplified when ligated, thus allowing for detection and quantification of miRNA biomarkers.

5. Methods of Treatment or Prevention

Compositions and methods of treating or preventing ESRD in a subject in need thereof are also featured in the invention.

In one embodiment, the present invention provides methods of treating such a subject who has been identified according to the methods described herein as having a risk of developing ESRD, e.g., elevated levels of let-7b-5p and/or miR-21-5p. In other embodiments, a subject having a disorder associated with chronic kidney disease may be treated using the methods described herein without having been identified by the predictive methods of the invention. Accordingly, in one embodiment, the invention relates to a method of treating a subject who has been identified as being at risk for developing ESRD, comprising determining the relative level of a progressor miRNA in a sample from the subject, wherein a higher level of the progressor miRNA in the sample relative to a non-progressor control level of the progressor miRNA or a normoalbuminuric control level of the progressor miRNA indicates that the subject is at risk of developing ESRD, and administering a therapeutically effective amount of an miRNA agent to the subject. In another embodiment, the invention relates to a method of treating or preventing ESRD in a subject, said method comprising administering to the subject an effective amount of a protective miRNA agent, such that ESRD in the subject is treated or prevented.

Therapeutic agents useful in the invention include, but are not limited to, an antagonist of let-7b-5p; an antagonist of miR-21-5p; a let-7c-5p agent; and/or a miR-29a-3p agent to the subject.

In certain embodiments, the subject is an ESRD progressor who would benefit either from the protective features of the miRNAs described herein and/or antagonist of the progression miRNAs described herein. Thus, the invention includes administering a let-7c-5p agent to a subject who is an ESRD progressor. Examples of let-7c-5p agents include, but are not limited to, let-7c-5p, a let-7c-5p mimic, a synthetic let-7c-5p oligonucleotide, and an expression vector encoding let-7c-5p. Alternatively, or in combination, the invention includes administering a miR-29a-3p agent to a subject who is an ESRD progressor. Example of miR-29a-3p agents include, but are not limited to, miR-29a-3p, a miR-29a-3p mimic, a synthetic miR-29a-3p oligonucleotide, and an expression vector encoding miR-29a-3p.

Renal fibrosis is the consequence of an excessive accumulation of extracellular matrix that occurs in virtually every type of chronic kidney disease. The pathogenesis of renal fibrosis is a progressive process that ultimately leads to end stage renal disease and failure. Accordingly, in another embodiment, the present invention provides methods of inhibiting the progression of renal fibrosis in a subject in need thereof, said method comprising administering to the subject an effective amount of an antagonist of an miRNA associated with renal fibrosis, such that renal fibrosis in the subject is inhibited. In one embodiment, the miRNA associated with renal fibrosis is selected from the group consisting of let-7b-5p and miR-21-5p. In another embodiment, the antagonist is an antisense inhibitor of the miRNA. In certain exemplary embodiments, the antisense inhibitor comprises a nucleic acid molecule that is at least 80% complementary to SEQ ID NO: 23 or SEQ ID NO: 24, for example a nucleic acid molecule that is at least 80%, 85%, 90%, 91%, 92%, 93%, 94%, 95%, 9%, 97%, 98% or 99% complementary to SEQ ID NO: 23 or SEQ ID NO: 24. The method of inhibiting renal fibrosis may, in certain embodiments, comprise administering an anti-fibrotic drug, such as pirfenidone, to the subject as a combination treatment to prevent or treat ESRD.

In one embodiment, the subject is a rapid progressor. In further embodiments, the subject has diabetes or high blood pressure.

The methods of the invention also include, in certain embodiments, administering an additional agent to the subject, for example an anti-fibrosis agent. Exemplary agents include, but are not limited to angiotensin-converting enzyme inhibitors (ACEI) and angiotensin II receptor type 1 blockers (ARB), renin inhibitors (aliskiren, enalkiren, zalkiren), mineralocorticoid receptor blockers (spironolacton, eplerenone), vasopeptidase inhibitors (e.g. AVE7688, omapatrilat).

The miRNA nucleic acid molecules useful in the therapeutic methods described herein may be synthetic. The term "synthetic" means the nucleic acid molecule is isolated and not identical in sequence (the entire sequence) and/or chemical structure to a naturally-occurring nucleic acid molecule, such as an endogenous precursor miRNA molecule. While in some embodiments, nucleic acids of the invention do not have an entire sequence that is identical to a sequence of a naturally-occurring nucleic acid, such molecules may encompass all or part of a naturally-occurring sequence. It is contemplated, however, that a synthetic nucleic acid administered to a cell may subsequently be modified or altered in the cell such that its structure or sequence is the same as non-synthetic or naturally occurring nucleic acid, such as a mature miRNA sequence. For example, a synthetic nucleic acid may have a sequence that differs from the sequence of a precursor miRNA, but that sequence may be altered once in a cell to be the same as an endogenous, processed miRNA. The term "isolated" means that the nucleic acid molecules of the invention are initially separated from different (in terms of sequence or structure) and unwanted nucleic acid molecules such that a population of isolated nucleic acids is at least about 90% homogeneous, and may be at least about 95, 96, 97, 98, 99, or 100% homogenous with respect to other polynucleotide molecules. In many embodiments of the invention, a nucleic acid is isolated by virtue of it having been synthesized in vitro separate from endogenous nucleic acids in a cell. It will be understood, however, that isolated nucleic acids may be subsequently mixed or pooled together.

It is understood that a "synthetic nucleic acid" of the invention means that the nucleic acid does not have a chemical structure or sequence of a naturally occurring nucleic acid. Consequently, it will be understood that the term "synthetic miRNA" refers to a "synthetic nucleic acid" that functions in a cell or under physiological conditions as a naturally occurring miRNA.

A nucleic acid may be made by any technique known to one of ordinary skill in the art, such as for example, chemical synthesis, enzymatic production or biological production.

Nucleic acid synthesis is performed according to standard methods. See, for example, Itakura and Riggs (1980). Additionally, U.S. Pat. Nos. 4,704,362, 5,221,619, and 5,583,013 each describe various methods of preparing synthetic nucleic acids. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR (see for example, U.S. Pat. Nos. 4,683,202 and 4,682,195, each incorporated herein by reference), or the synthesis of an oligonucleotide described in U.S. Pat. No. 5,645,897, incorporated herein by reference.

Oligonucleotide synthesis is well known to those of skill in the art. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

Recombinant methods for producing nucleic acids in a cell are well known to those of skill in the art. These include the use of vectors, plasmids, cosmids, and other vehicles for delivery a nucleic acid to a cell, which may be the target cell or simply a host cell (to produce large quantities of the desired RNA molecule). Alternatively, such vehicles can be used in the context of a cell free system so long as the reagents for generating the RNA molecule are present. Such methods include those described in Sambrook, 2003, Sambrook, 2001 and Sambrook, 1989, which are hereby incorporated by reference.

In certain embodiments, the nucleic acid molecules of the present invention are not synthetic. In some embodiments, the nucleic acid molecule has a chemical structure of a naturally occurring nucleic acid and a sequence of a naturally occurring nucleic acid, such as the exact and entire sequence of a single stranded primary miRNA (see Lee 2002), a single-stranded precursor miRNA, or a single-stranded mature miRNA. In addition to the use of recombinant technology, such non-synthetic nucleic acids may be generated chemically, such as by employing technology used for creating oligonucleotides.

The present invention involves in some embodiments delivering a nucleic acid into a cell. This may be related to a therapeutic or diagnostic application.

The polynucleotide may be incorporated within a variety of macromolecular assemblies or compositions. Such complexes for delivery may include a variety of liposomes, nanoparticles, and micelles, formulated for delivery to a patient. The complexes may include one or more fusogenic or lipophilic molecules to initiate cellular membrane penetration. Such molecules are described, for example, in U.S. Pat. Nos. 7,404,969 and 7,202,227, which are hereby incorporated by reference in their entireties.

The composition or formulation may employ a plurality of therapeutic polynucleotides, each independently as described herein. For example, the composition or formulation may employ from 1 to 5 miRNA inhibitors and/or miRNA mimetics.

The polynucleotides of the invention may be formulated as a variety of pharmaceutical compositions. Pharmaceutical compositions will be prepared in a form appropriate for the intended application. Generally, this will entail preparing compositions that are essentially free of pyrogens, as well as other impurities that could be harmful to humans or animals. Exemplary delivery/formulation systems include colloidal dispersion systems, macromolecule complexes, nanocapsules, microspheres, beads, and lipid-based systems including oil-in-water emulsions, micelles, mixed micelles, and liposomes. Commercially available fat emulsions that are suitable for delivering the nucleic acids of the invention to cardiac and skeletal muscle tissues include Intralipid, Liposyn, Liposyn II, Liposyn III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. Nos. 5,981,505; 6,217,900; 6,383,512; 5,783,565; 7,202,227; 6,379,965; 6,127,170; 5,837,533; 6,747,014; and WO03/093449, which are hereby incorporated by reference in their entireties.

The pharmaceutical compositions and formulations may employ appropriate salts and buffers to render delivery vehicles stable and allow for uptake by target cells. Aqueous compositions of the present invention comprise an effective amount of the delivery vehicle comprising the inhibitor polynucleotides or miRNA polynucleotide sequences (e.g. liposomes or other complexes), dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" may include one or more solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Supplementary active ingredients also can be incorporated into the compositions.

Administration or delivery of the pharmaceutical compositions according to the present invention may be via any route so long as the target tissue is available via that route. For example, administration may be by intradermal, subcutaneous, intramuscular, intraperitoneal or intravenous injection, or by direct injection into target tissue (e.g., cardiac tissue). Pharmaceutical compositions comprising miRNA inhibitors or expression constructs comprising miRNA sequences may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. Nos. 6,416,510; 6,716,196; 6,953,466, WO 2005/082440, WO 2006/089340, U.S. Patent Publication No. 2007/0203445, U.S. Patent Publication No. 2006/0148742, and U.S. Patent Publication No. 2007/0060907, which are all hereby incorporated by reference in their entireties.

The compositions or formulations may also be administered parenterally or intraperitoneally. By way of illustration, solutions of the conjugates as free base or pharmacologically acceptable salts can be prepared in water suitably mixed with a surfactant, such as hydroxypropylcellulose.

Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by their use in the compositions of agents delaying absorption, for example, aluminum monostearate and gelatin.

Sterile injectable solutions may be prepared by incorporating the conjugates in an appropriate amount into a solvent along with any other ingredients (for example as enumerated above) as desired. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The invention is further illustrated by the following examples, which should not be construed as limiting. The entire contents of all references, patents and published patent applications cited throughout this application are hereby incorporated by reference in their entirety.

EXAMPLES

The examples described herein examine the concentrations of circulating miRNAs involved in the TGF-β1 pathway in type 1 diabetes (T1D) patients who had normal renal function but were shown prospectively to be at extreme risk of rapid progression to ESRD (see references 24-28 for research relating to the role of both circulating and urinary miRNAs in DN). As described below in Examples 1 to 4, concentrations of circulating miRNAs involved in the TGF-β1 pathway were examined in T1D patients who had normal renal function but were shown prospectively to be at extreme risk of rapid progression to ESRD.

Research Design and Methods

The following research design and methods relate to the study described in Examples 1 to 4.

Study Subjects

All subjects included in this study were recruited while attending the Joslin Clinic in Boston, Mass., using protocols and consent procedures approved by the Joslin Diabetes Center Institutional Review Board. All patients had baseline examinations that included standardized measurements of blood pressure and the collection of peripheral blood.

The proteinuric patients included in this study are members of the Joslin Proteinuria Cohort (29; 30). Briefly, this cohort was ascertained between 1991 and 2004 from among ~3,500 adult T1D patients receiving long-term care at the Joslin Clinic during this period and was followed through 2011. All patients enrolled to this cohort were Caucasian and had persistent proteinuria, defined by a urinary albumin-to-creatinine ratio (ACR)≥300 μg/mg in two of the last three measurements taken at least one month apart. The description of clinical characteristics for this cohort has previously been published (29; 30). Serum creatinine concentration and the Chronic Kidney Disease Epidemiology Collaboration formula were used to estimate renal function (eGFR) at study entry and during follow-up (31). For each patient, serial measures of serum creatinine were used to estimate the rate of eGFR decline (eGFR slopes) during this follow-up period using a general linear model as described by Skupien et al. (30). For the present study, 38 proteinuric patients were identified with normal renal function (eGFR≥60 ml/min per 1.73 m$^2$) at enrollment and with the fastest rate of eGFR decline (i.e., rapid progressors). As a result of this rapid eGFR loss, the majority of these patients developed ESRD or reached CKD stage 4 during first 10 years of follow-up. From this same cohort, 38 patients were selected who maintained normal and stable renal function over the course of the follow-up period despite persistent proteinuria (i.e., non-progressors).

Additionally, 40 T1D patients with normoalbuminuria who maintained normal and stable renal function during 4-10 years of follow-up were randomly selected from the 2$^{nd}$ Joslin Kidney Study as a healthy reference sub-group (i.e., normoalbuminuric controls) (32). Briefly, the 2$^{nd}$ Joslin Kidney Study is a longitudinal investigation on the natural history of early diabetic nephropathy in non-proteinuric patients (determined by at least two ACR measurements during their 2 clinical visits preceding enrollment) with T1D attending the Joslin Clinic between 2003 and 2006. Within this cohort, 364 patients entered the study with normoalbuminuria and a median duration of T1D of more than 20 years. Among these patients, 249 had an HbA1c persistently above 7.4%, yet maintained their normoalbuminuria and normal and stable renal function during 4-10 years of follow-up. Forty normoalbuminuric controls were randomly selected from this group to serve as a healthy reference sub-group for the present study.

RNA Isolation from Plasma Specimens

Peripheral blood was collected in EDTA tubes from all patients included in this study at the time of their enrollment. Briefly, all blood samples were centrifuged at 3,000 g for 10 minutes. Plasma supernatant was then aliquoted into ribonuclease-free tubes and stored at −80° C. until analysis.

Plasma specimens from the 40 normoalbuminuric controls selected for this study were pooled and used for experiments to determine the baseline levels of TGF-β-regulated miRNAs in patients with T1D. Individual plasma specimens from these same normoalbuminuric patients, 38 rapid progressors, and 38 non-progressors were used to isolate total RNA for determination of the levels of TGF-β-regulated miRNAs. Because of limited baseline sample availability, individual plasma samples collected during the follow-up period were used for the 38 non-progressors included in this study. Importantly, the rate of eGFR decline maintained by these patients throughout their follow-up and at the time of the collection the plasma samples used in this study was less than 3.3 ml/min per 1.73 $m^2$ per year.

Total RNA was isolated from 180 µl of pooled plasma from 40 normoalbuminuric controls and 100 µl from individual plasma from 40 normoalbuminuric controls, 38 rapid progressors, and 38 non-progressors using the Qiagen's miRNeasy Serum/Plasma Kit (Qiagen, Valencia, Calif.).

For the pooled plasma sample from normoalbuminuric controls, 900 µl of QIAzol reagent was added to 180 µl of plasma followed by the addition of 3.5 µl of $1.6\times10^8$ copies/µl of a synthetic C. elegans miRNA (cel-miR-39-3p) exogenous normalization control. In the absence of established endogenous control miRNAs for normalization in human plasma, spiked-in RNAs, such as cel-miR-39-3p, have been shown to serve as stable reference normalization controls (19; 33; 34). The sample was then mixed thoroughly followed by the addition of 180 µl of chloroform. After vortexing for 15 seconds, the sample was centrifuged at 12,000 g for 15 minutes at 4° C. The aqueous phase containing the RNA was then transferred to a new collection tube, combined with 1.5 volumes of 100% ethanol, applied to the silica membrane of a miRNeasy MiniElute Spin column (Qiagen), and centrifuged at 10,000 g for 15 seconds at room temperature. The retained RNA was then washed using buffers provided with the miRNeasy Serum/Plasma Kit. First, 700 µl Buffer RWT was applied to the spin column, followed by centrifugation at 10,000 g for 15 seconds at room temperature. Next, 500 µl Buffer RPE was added, followed by centrifugation at 10,000 g for 15 seconds at room temperature. The spin column was then washed with 500 µl of 80% ethanol, incubated at room temperature for 2 minutes, and centrifuged for 2 minutes at 10,000 g at room temperature. High speed centrifugation (20,000 g) was performed for 5 minutes at room temperature to dry the silica membrane. RNA was eluted by applying 14 µl RNase-free water to the membrane followed by a 2 minute incubation at room temperature and high speed centrifugation for 1 minute. The isolated RNA was stored at −80° C. until further processing.

RNA isolation from all individual plasma samples was performed as described above with the following exceptions: 500 µl of QIAzol reagent was added to 100 µl of plasma followed by the addition of 3.5 µl of $1.6\times10^8$ copies/µl of cel-miR-39-3p, all samples were then mixed thoroughly, followed by the addition of 100 µl of chloroform. All isolated RNA samples were stored at −80° C. until further processing.

miRNome Profiling in Pooled T1D Normoalbuminuric Controls Sample

Reverse transcription of RNA isolated from pooled plasma from T1D normoalbuminuric controls was performed using the miScript II RT Kit with miScript HiSpec Buffer (Qiagen). 6 µl of isolated RNA from the pooled normoalbuminuric controls sample was used to prepare a 10 µl reverse transcription reaction as specified by the manufacturer. This was then incubated at 37° C. for 60 minutes followed by 95° C. for 5 minutes using a PTC-200 thermal cycler (MJ Research, Watertown, Mass.). The prepared cDNA was diluted 5 times using RNase-free water and stored at −20° C. prior to further processing.

Because small volumes of human plasma contain low amounts of RNA, pre-amplification of target miRNAs prior to quantification is required to accurately assess their expression. Highly multiplexed, PCR-based pre-amplification reactions were performed using Qiagen's miScript Pre-amp PCR Kit. As this kit amplifies up to 400 miRNA-specific cDNA targets in a single reaction, pre-amplification of the miRNAs included on Qiagen's miScript miRNA PCR Array Human miRNome (V16.0, 384-well; includes 1,066 miRNAs distributed over 3 384-well plates) was performed in 3 separate pre-amplification reactions using miScript PreAMP miRNome Primer Mixes (MBHS-16AZ, MBHS-16BZ, and MBHS-16CZ, respectively). For each reaction, 5 µl of diluted cDNA from the pooled normoalbuminuric controls sample was used in a 25 µl pre-amplification reaction using miScript PreAMP PCR Kit. Pre-amplification was performed using a PTC-200 thermal cycler and the following cycling conditions: 95° C. for 15 minutes, 2 cycles of 94° C. for 30 seconds, 55° C. for 1 minute, and 70° C. for 1 minute, and 10 cycles of 94° C. for 30 seconds and 60° C. for 1 minute. As per the manufacturer's recommendation, the pre-amplified cDNA from these 3 reactions were pooled together then diluted 5-fold using RNase-free water prior to being stored at −20° C.

Following reverse transcription and pre-amplification, the levels of 1,066 miRNAs included on the miScript miRNA PCR Array Human miRNome were assayed in the pooled normoalbuminuric control sample by SYBR Green-based qRT-PCR using 0.25 µl of diluted cDNA in a 10 µl reaction on an ABI 7900HT Fast Real-Time PCR System (Applied Biosystems, Foster City, Calif.). The following 3-step cycling program was used: 95° C. for 15 minutes and 40 cycles of 94° C. for 15 seconds, 55° C. for 30 seconds, and 70° C. for 30 seconds. Amplification results were analyzed with the SDS 2.4 software (Applied Biosystems). miRNome profiling of the pooled normoalbuminuric T1D control sample was performed in duplicate.

TGF-β-Regulated miRNA Analysis in Individual Plasma Samples

Profiling of 5 highly-detectable TGF-β-regulated miRNAs (let-7b-5p, let-7c-5p, miR-21-5p, miR-29a-3p, and miR-29c-3p), along with cel-miR-39-3p and two proprietary Qiagen controls used to assess the efficiency of reverse transcription (miRTC and PPC), was performed using a custom miScript miRNA PCR array from Qiagen in individual plasma specimens from 38 rapid progressors, 38 non-progressors, and 40 normoalbuminuric controls. Prior to quantification, reverse transcription of RNA from all individual samples was performed using fixed volumes of isolated RNA (1.5 μl for each individual sample) and the miScript II RT Kit with miScript HiSpec Buffer (Qiagen) as described above.

Pre-amplification of let-7b-5p, let-7c-5p, miR-21-5p, miR-29a-3p, and miR-29c-3p, along with cel-miR-39-3p and two proprietary Qiagen controls used to assess the efficiency of reverse transcription (miRTC and PPC), was performed using diluted cDNA from 38 rapid progressors, 38 non-progressors, and 40 normoalbuminuric controls, the miScript PreAMP PCR Kit, and a custom miScript PreAMP Primer Mix. For each sample, 5 μl of diluted cDNA was used in a 25 μl pre-amplification reaction as described above. The pre-amplified cDNAs were then diluted 20-fold using RNase-free water prior and stored at −20° C.

Profiling of let-7b-5p, let-7c-5p, miR-21-5p, miR-29a-3p, miR-29c-3p, and cel-miR-39-3p was performed using pre-amplified cDNA from these samples and a custom miScript miRNA PCR Array. SYBR Green-based qRT-PCR was performed in duplicate using an ABI 7900HT Fast Real-Time PCR System as described above. Amplification results were analyzed with the SDS 2.4 software.

Statistical Analysis

All statistical analyses were conducted in SAS for Windows, version 9.2 (SAS Institute, Cary, N.C.). Differences in clinical characteristics between study groups were tested using Student's t-test and a $\chi^2$ test for continuous and categorical variables, respectively.

Cel-miR-39 was used for normalization to obtain relative levels of each TGF-β-regulated miRNA according to the equation $2^{-\Delta cq}$, where $\Delta$ Cq=average $Cq_{TGF\text{-}\beta 1\text{-}regulated\ miRNA}$ −average $Cq_{cel\text{-}miR\text{-}39}$. Group-wise comparisons of differences in TGF-β1-regulated miRNA levels were first assessed by nonparametric Kruskal-Wallis and Mann-Whitney tests, as appropriate. The effects of TGF-β1-regulated miRNA on the risk of rapid loss of renal function/the risk of proteinuria were then assessed using univariable and multivariable logistic regression analysis. Effect measures were expressed as the odds ratios per 1 standard deviation increase of normalized miRNA relative level. Multivariable analyses were adjusted for gender, age, $HbA_{1c}$, and duration of T1D. P-values <0.01 (0.05/5 miRNAs) were considered statistically significant.

Example 1: Study Groups and Clinical Characteristics

Clinical characteristics for the rapid progressors, non-progressors, and normoalbuminuric controls included in this study are summarized in the Table 1, below. In Table 1, data are means±SD unless otherwise indicated. All clinical characteristics are from baseline examinations with the exception of eGFR slope. BP, blood pressure; NP, nonprogressors; RP, rapid progressors. Rapid progressors were observed throughout the duration of the follow-up period or until they reached ESRD. As plasma specimens from nonprogressors collected at entry to the study were limited, plasma samples collected during the follow-up period were used in this study. The duration of follow-up provided for nonprogressors corresponds to the time from the collection of the sample used in this study to the end of follow-up. As shown in Table 1, thirty-three out of 38 (86.8%) patients reached ESRD during the follow-up period, 1 patient progressed to CKD stage 4, and the remaining 4 patients lost 50% of their baseline eGFR prior to being lost to follow-up.

TABLE 1

| Clinical Characteristic | Rapid Progressors (RP; N = 38) | Non-Progressors | Normoalbuminuric Controls (N = 40) | p-values (RP vs. NP) |
|---|---|---|---|---|
| Men (%) | 44.7 | 73.7 | 35.0 | 0.01 |
| Age of diabetes diagnosis (years) | 13 ± 9.0 | 11.3 ± 6.3 | 13.6 ± 7.1 | 0.33 |
| Duration of diabetes (years) | 22.1 ± 9.0 | 30.8 ± 9.3 | 18.3 ± 7.5 | <0.0001 |
| Age (years) | 35.1 ± 7.8 | 42.1 ± 7.8 | 31.8 ± 10.4 | 0.0002 |
| $HbA_{1c}$ (%) | 10.0 ± 1.6 | 9.6 ± 1.3 | 8.6 ± 1.0 | 0.17 |
| Systolic blood pressure (mmHg) | 132.4 ± 18.1 | | | 0.02 |
| Diastolic blood pressure (mmHg) | 81.3 ± 9.9 | | | 0.57 |
| ACR (μg/mg), median (25th, 75th percentiles) | 1041.5 (385.4, 2015.4) | 496.8 (313.4, 868.3) | 12.4 (10.5, 15.2) | 0.0005 |
| Baseline eGFR (ml/min per 1.73 m²), median (25th, 75th percentiles) | 100.3 (79.0, 115.3) | 95.0 (80.7, 112.1) | 116.5 (104.5, 126.4) | 0.49 |
| Duration of follow up (years) | 5.1 ± 2.8* | 11.1 ± 5.0† | 7.4 ± 1.6 | <0.0001 |
| Last follow up eGFR, median (25th, 75th percentiles) | —‡ | 87.2 (69.5, 103.5) | 112.8 (100.0, 120.6) | — |

TABLE 1-continued

| Clinical Characteristic | Rapid Progressors (RP; N = 38) | Non-Progressors | Normoalbuminuric Controls (N = 40) | p-values (RP vs. NP) |
|---|---|---|---|---|
| eGFR slope (ml/min per 1.73 m² per year) | −20.7 ± 14.8 | −1.02 ± 0.9 | −0.77 ± 1.1 | <0.0001 |

Clinical characteristics are presented as mean values ± standard deviation unless otherwise specified. All clinical characteristics are from baseline examinations with the exception of eGFR slope.
*Rapid progressors were observed throughout the duration of the follow-up period or until they reached ESRD.
†As plasma specimens from non-progressors collected at entry to the 2$^{nd}$ Joslin Kidney Study were limited, plasma samples collected during the follow-up period were used in this study. The duration of follow-up provided for non-progressors corresponds to the time from the collection of the sample used in this study to the end of follow-up.

In comparison with the rapid progressor group, non-progressors included more male subjects, had a longer duration of T1D, were older at baseline, and had higher systolic blood pressure. By design, both patient groups had urinary ACRs in the proteinuric range, although this was lower in non-progressors. Both subgroups also had normal baseline eGFR. During follow-up, eGFR declined rapidly in the rapid progressors such that within 3-11 years nearly all had either developed ESRD or reached chronic kidney disease (CKD) stage 4. All non-progressors had no or minimal renal function loss during 7-20 years of follow-up; the majority were in CKD stage 1-2 at their last follow-up.

Normoalbuminuric controls included fewer males and were younger than the non-progressor group and had the lowest blood pressure, HbA1c, and ACR levels relative to both rapid progressors and non-progressors. Baseline eGFR was also higher among patients in this group compared to both rapid progressors and non-progressors and their rate of eGFR loss was minimal and similar to that observed in non-progressors.

Example 2: Levels of Candidate TGF-β1-Regulated miRNAs in Plasma from T1D Patients Previous studies have shown that several miRNAs, including let-7a/b/c, miR-2a, miR-21, the miR-29 family, miR-192, the miR-200 family, miR-215, miR-216a, miR-217, miR-377, miR-382, and miR-491, are altered in response to TGF-β1 in vitro or in various animal models (10-18; 35-44). To establish the detectability of these and other miRNAs in plasma from T1D patients, 1,066 miRNAs included on Qiagen's miScript miRNA PCR Array Human miRNome in a pooled plasma sample derived from 40 healthy T1D normoalbuminuric patients were profiled as described above. Among 22 TGF-β1-regulated miRNAs identified in the literature, 12 of these miRNAs were found to be highly detectable (defined as a Cq value ≤30) in plasma from these patients, listed in Tables 2 and 4 below.

TABLE 2

| miRNA | Cq |
|---|---|
| let-7b-3p | 28.66 |
| miR-29b-3p | 26.19 |
| miR-29b-1-5p | 29.52 |
| miR-200a-5p | 29.44 |
| miR-200c-3p | 29.95 |
| miR-377-3p | 29.33 |
| miR-382-5p | 27.20 |
| miR-192-5p | 27.37 |
| miR-491-5p | 29.78 |

The TGF-β1-regulated miRNAs that were not detected in the pooled sample are listed in Table 3 below.

TABLE 3

| miRNA | Cq |
|---|---|
| miR-21-3p | 30.13 |
| miR-29a-5p | 32.63 |
| miR-29b-2-5p | 33.96 |
| miR-29c-5p | 30.31 |
| miR-141-3p | 31.84 |
| miR-141-5p | 33.88 |
| miR-192-3p | 31.21 |
| miR-200a-3p | 32.35 |
| miR-200b-3p | 31.09 |
| miR-200b-5p | 30.46 |
| miR-200c-5p | 32.70 |
| miR-215-5p | 32.05 |
| miR-216a-5p | 33.75 |
| miR-216b-5p | 33.25 |
| miR-217 | 31.78 |
| miR-296-5p | 30.97 |
| miR-298 | 33.23 |
| miR-377-5p | 31.42 |
| miR-382-3p | >35.00 |

Example 3. Association of Plasma TGF-β1-Regulated miRNAs with the Risk of Rapid Progression to ESRD To explore the relationship between plasma TGF-β1-regulated miRNAs and the risk of rapid progression to ESRD, the 5 most highly-detectable TGF-β1-regulated miRNAs identified in the normoalbuminuric control sample were chosen for further examination, as shown in Table 4, below. Table 4 shows a summary of TGF-β1-regulated miRNAs detected in plasma from normoalbuminuric control subjects who were selected for examination in rapid progressors and nonprogressors

TABLE 4

| miRNA | Cq | Reported TGF-β1 Effect on miRNA Expression | Reference(s) |
|---|---|---|---|
| let-7b-5p | 24.23 | Down-regulated | Wang et al . . . , 2014 |
| let-7c-5p | 25.67 | Down-regulated | Brennen et al . . . , 2013 |
| miR-21-5p | 19.88 | Up-regulated | Zhong et al . . . , 2011 |
| miR-29a-3p | 22.53 | Down-regulated | Du et al . . . , 2010; Qin et al . . . , 2011; Wang et al . . . , 2012 |
| miR-29c-3p | 21.79 | Down-regulated | Qin et al . . . , 2011; Wang et a., 2012 |

As described above, the level of these five miRNAs was examined in baseline plasma specimens from 38 T1D patients at risk of rapid progression to ESRD (rapid progressors) and 38 T1D patients determined to have stable renal function (non-progressors) that have been followed longitudinally at the Joslin Clinic.

Of the 5 TGF-β-related miRNA that were assayed, let-7c-5p and miR-29a-3p were highly detectable in plasma collected from patients included in this study and had Cq values similar to this exogenous control (ranging from 13.4 to 19.9). The 3 additional miRNAs (let-7b-5p, miR-21-5p, and miR-29c-3p), while detectable, were present in much lower abundance than the endogenous control miRNA, let-7c-5p, and miR-29a-3p (Cq values ranging from 25.6 to 32.6).

FIG. 1 shows the relative levels of TGF-β1-regulated miRNAs in plasma from rapid progressors, non-progressors, and normoalbuminuric controls. Normalized relative levels of each miRNA are presented in the form 2-ΔCq and cel-miR-39-3p was used as a stable reference normalization control. RP=rapid progressors, NP=non-progressors, and NA=normoalbuminuric controls.

Table 5, below shows the results of analysis of circulating TGF-β1-regulated miRNA levels in rapid progressors, non-progressors, and normoalbuminuric control subjects. The relative levels of let-7b-5p, let-7c-5p, miR-21-5p, miR-29a-3p, and miR-29c-3p were significantly different among patients with proteinuria who either lost (i.e., rapid progressors) or maintained renal function (i.e., non-progressors) over the follow-up period and normoalbuminuric controls (Kruskal-Wallis P≤0.0003 (see Table 5). Mann-Whitney U test P-values from comparisons between rapid progressors and non-progressors are provided.

TABLE 6

| miRNA | let-7b-5p | let-7c-5p | miR-21-5p | miR-29a-3p | miR-29c-3p |
|---|---|---|---|---|---|
| let-7b-5p | 1 | 0.08 | 0.74 | 0.04 | 0.61 |
| let-7c-5p |  | 1 | −0.10 | 0.83 | 0.18 |
| miR-21-5p |  |  | 1 | 0.03 | 0.65 |
| miR-29a-3p |  |  |  | 1 | 0.26 |
| miR-29c-3p |  |  |  |  | 1 |

These data suggest that 4 of the miRNAs examined in this study (let-7b-5p, let-7c-5p, miR-21-5p, and miR-29a-3p) are associated with the risk of rapid renal function decline experienced by rapid progressors, while miR-29c-3p, on the other hand, is associated with an increased risk of proteinuria. These relationships, and the effects of these miRNAs on these two phenotypes, were further assessed using logistic regression analysis.

For analyses of the miRNAs associated with rapid progression to ESRD, miRNA levels between the two non-decliner patient groups (i.e., non-progressors and normoalbuminuric controls) and rapid progressors were compared. Table 7 shows logistic regression analysis of circulating TGF-β1-regulated miRNA levels and the risk of rapid progression to ESRD

TABLE 5

| | Relative miRNA Levels (Mean ± SD)* | | | Kruskal-Wallis ANOVA P-values | Mann-Whitney U Test P-values (RP vs. NP) |
|---|---|---|---|---|---|
| miRNA | Rapid Progressors (RP) | Non-Progressors (NP) | Normoalbuminuric Controls | | |
| let-7b-5p | $8.0 \times 10^{-4} \pm 9.8 \times 10^{-4}$ | $3.4 \times 10^{-4} \pm 4.2 \times 10^{-4}$ | $1.9 \times 10^{-4} \pm 2.6 \times 10^{-4}$ | 0.0003 | 0.01 |
| let-7c-5p | 1.7 ± 1.6 | 3.1 ± 2.1 | 3.7 ± 2.7 | <0.0001 | 0.0002 |
| miR-21-5p | $9.9 \times 10^{-4} \pm 1.4 \times 10^{-3}$ | $2.2 \times 10^{-4} \pm 3.8 \times 10^{-4}$ | $5.6 \times 10^{-5} \pm 6.0 \times 10^{-5}$ | <0.0001 | 0.006† |
| miR-29a-3p | 2.17 ± 3.05 | 3.5 ± 2.4 | 4.2 ± 2.7 | <0.0001 | 0.0007 |
| miR-29c-3p | $1.1 \times 10^{-3} \pm 1.3 \times 10^{-3}$ | $1.3 \times 10^{-3} \pm 1.8 \times 10^{-3}$ | $6.2 \times 10^{-4} \pm 1.2 \times 10^{-3}$ | 0.0003 | 0.68‡ |

*The relative level of each miRNA was calculated according to the equation $2^{-\Delta Cq}$, where $\Delta Cq = \text{average } Cq_{TGF\text{-}\beta1\text{-}regulated\ miRNA} - \text{average } Cq_{cel\text{-}miR\text{-}39}$.
†miR-21-5p was significantly up-regulated in both rapid progressors (P < 0.0001) and non-progressors (P = 0.02) compared to normoalbuminuric controls.
‡The relative level of miR-29c-3p did not differ between rapid progressors and nonprogressors, however, this miRNA was significantly increased in both rapid progressors (P = 0.0009) and nonprogressors (P = 0.0003) compared with normoalbuminuric control subjects.

Of these, let-7b-5p and miR-21-5p were found to be significantly up-regulated in rapid progressors relative to non-progressors (P=0.01 and P=0.006, respectively). Table 6 shows the Spearman rank order correlation coefficients between TGF-β1-regulated miRNA levels. Both let-7b-5p and miR-21-5p miRNAs were found to be highly correlated (Spearman's p≤0.74; Table 6). Conversely, while also highly correlated with each other (Spearman's p≤0.83; Table 6), let-7c-5p and miR-29a-3p were significantly down-regulated in rapid progressors compared to non-progressors (P=0.0002 and P=0.0007, respectively). The relative level of miR-29c-3p did not differ between rapid progressors and non-progressors (P=0.68). This miRNA was, however, significantly increased in these 2 patient groups relative to normoalbuminuric controls (P=0.0009 and P=0.0003, respectively).

TABLE 7

| | Unadjusted | | Adjusted‡ | |
|---|---|---|---|---|
| miRNA | Odds Ratios (95% CI)† | P-values | Odds Ratios (95% CI)† | P-values |
| let-7b-5p | 2.51 (1.42, 4.43) | 0.002 | 2.38 (1.31, 4.06) | 0.004 |
| let-7c-5p | 0.23 (0.10, 0.52) | 0.0004 | 0.23 (0.10, 0.53) | 0.0006 |
| miR-21-5p | 6.33 (1.75, 22.92) | 0.005 | 5.87 (1.68, 20.46) | 0.006 |
| miR-29a-3p | 0.38 (0.20, 0.74) | 0.004 | 0.39 (0.20, 0.76) | 0.00.6 |

*The Rapid Progressor group is the reference group. To estimate the effects of these miRNAs on rapid progression to ESRD, Rapid Progressors were compared with the combined non-progressor group (i.e., Non-Progressors and Normoalbuminuric Controls).
†Effect measures are expressed as the odds ratios per SD increase of normalized relative miRNA level.
‡Multivariable analyses were adjusted for gender, age, $HbA_{1c}$, and duration of T1D.

In univariable analyses, the odds ratios (OR) for the risk of rapid progression to ESRD for a 1 SD increase in the relative level of plasma let-7b-5p was 2.51 (95% confidence interval (CI): 1.42, 4.43; P=0.002). Similarly, a 1 SD increase in the relative plasma level of miR-21-5p was associated with a 6.3 fold increase in the risk of rapid progression to ESRD (OR=6.33, 95% CI: 1.75, 22.92; P=0.005). For both let-7c-5p and miR-29a-3p, a 1 SD increase in their relative plasma levels was associated with more than a 50% reduction in the risk of rapid progression to ESRD (OR=0.23, 95% CI: 0.10, 0.52; P=0.0004 and OR=0.38, 95% CI: 0.20, 0.74; P=0.004, respectively). The strength of each of these associations was not diminished following adjustments for gender, age, $HBA1_c$, and duration of T1D.

Example 4. Association of Plasma TGF-β1-Regulated miRNAs with the Risk of Proteinuria In a logistic model to assess the effect of miR-29c-3p on the risk of proteinuria, the relative level of this miRNA's relative level in normoalbuminuric controls was compared with that in the two proteinuric patient groups (i.e., rapid progressors and non-progressors). Although not statistically significant, a 1 SD increase in the miRNA's plasma level was suggestive of a 1.7 fold increase in the risk of proteinuria (OR=1.73, 95% CI: 0.96, 3.10; P=0.07).

Summary of Examples 1-4

The study described in Examples 1-4 demonstrates that miRNAs involved in the TGF-β1 pathway are deregulated very early in T1D patients who are at risk of rapid progression to ESRD. The above examples provide an extensive analysis of circulating miRNAs in plasma specimens. A major strength of the study design described herein over previous studies is its use of a well-characterized cohort of T1D patients that have been followed longitudinally over the course of 7-15 years of follow-up.

The study described in Examples 1-4 investigated whether circulating TGF-β1-regulated miRNAs detectable in plasma are associated with the risk of rapid progression to ESRD in a cohort of proteinuric patients with T1D and normal eGFR. Plasma specimens obtained at entry to the study were examined in two prospective sub-groups that were followed for 7-20 years (rapid progressors and non-progressors), as well as a reference panel of normoalbuminuric T1D patients.

Of the 5 miRNAs examined in this study, let-7c-5p and miR-29a-3p were significantly associated with protection against rapid progression and let-7b-5p and miR-21-5p were significantly associated with the increased risk of ESRD. In logistic analysis, controlling for HbA1c and other covariates, let-7c-5p and miR-29a-3p were associated with more than a 50% reduction in the risk of rapid progression (P≤0.001), while let-7b-5p and miR-21-5p were associated with a >2.5-fold increase in the risk of ESRD (P≤0.005).

The findings described herein show that plasma let-7b-5p and miR-21-5p are associated with an increased risk of rapid progression to ESRD in patient with T1D are supported by data from a number of prior in vitro and in vivo studies of DN (15; 16; 18; 37; 45; 46). Both let-7b-5p and miR-21-5p have been shown to target genes directly implicated in renal function decline. For example, in cultured human podocytes, Schaeffer et al. demonstrated that hyperglycemia-induced let-7b expression reduces levels of laminin-β2 (LAMB2), an extracellular matrix glycoprotein critical to normal podocyte function (46). Similarly, up-regulation of miR-21 has been reported to contribute to fibrotic scarring by directly targeting matrix metallopeptidase 9 (MMP-9) (15; 16; 18; 37; 45).

Interestingly, anti-miR-21 therapy decreases tissue inhibitor of metalloproteinase 1 (TIMP1), collagen IV, fibronectin protein levels, and reduces glomerular basement membrane thickening, suggesting that miR-21 is a potential therapeutic target against the progression of DN (15; 18).

In contrast to the findings for the majority of miRNA examined in this study, miR-29c-3p was not associated with either the risk of or protection against rapid progression to ESRD. This miRNA was, however, increased in patients with proteinuria, irrespective of renal function decline, relative to those with persistent normoalbuminuria. These empirical data challenge the conventional model that regards DN as a disease that advances sequentially through characteristic stages defined by increasing levels of albuminuria followed by the development of renal decline (47). Furthermore, this intriguing finding supports the hypothesis that albuminuria and renal decline are uncoupled phenotypes (32).

The above examples are based on a well-characterized cohort of T1D patients that have been followed longitudinally for more than a decade allows an assessment of the predictive utility of various biomarkers, including miRNAs, in determining which patients might be most at risk of or protected against rapid progression to ESRD. The findings described herein suggest that TGF-β1-regulated miRNAs detectable in plasma could be pre-clinical indicators of early renal decline and, therefore, might have utility in identifying patients most at risk of renal function decline and progression to ESRD. Therapeutic augmentation of these miRNAs may prove useful in inhibiting fibrogenesis and modifying the risk of renal function decline in T1D.

In sum, the present study examined the levels of five circulating TGF-β1-regulated miRNAs in baseline plasma specimens taken from T1D patients who were found to be either at risk for or protected against rapid progression to ESRD. The strongest association that we observed was with the protective effects of let-7c-5p. The study (Examples 1-4) is the first prospective study to demonstrate that circulating TGF-β1-regulated miRNAs are deregulated early in T1D patients who are at risk of rapid progression to ESRD.

TABLE 8

Sequence Listing

| miRNA | miRBase Accession No. | SEQ ID NO: |
|---|---|---|
| hsa-miR-10b-5p | MIMAT0000254 | UACCCUGUAGAACCGAAUUUGUG SEQ ID NO: 1 |
| hsa-miR-451a | MIMAT0001631 | AAACCGUUACCAUUACUGAGUU SEQ ID NO: 2 |
| hsa-miR-199a-5p | MIMAT0000231 | CCCAGUGUUCAGACUACCUGUUC SEQ ID NO: 3 |
| hsa-miR-3907 | MIMAT0018179 | AGGUGCUCCAGGCUGGCUCACA SEQ ID NO: 4 |
| hsa-miR-143-3p | MIMAT0000435 | UGAGAUGAAGCACUGUAGCUC SEQ ID NO: 5 |
| hsa-miR-19b-3p | MIMAT0000074 | UGUGCAAAUCCAUGCAAAACUGA SEQ ID NO: 6 |
| hsa-miR-22-5p | MIMAT0004495 | AGUUCUUCAGUGGCAAGCUUUA SEQ ID NO: 7 |
| hsa-miR-221-3p | MIMAT0000278 | AGCUACAUUGUCUGCUGGGUUUC SEQ ID NO: 8 |

TABLE 8-continued

Sequence Listing

| miRNA | miRBase Accession No. | | SEQ ID NO: |
|---|---|---|---|
| hsa-miR-24-3p | MIMAT0000080 | AGCUACAUUGUCUGCUGGGUUUC | SEQ ID NO: 9 |
| hsa-miR-4507 | MIMAT0019044 | CUGGGUUGGGCUGGGCUGGG | SEQ ID NO: 10 |
| hsa-miR-4539 | MIMAT0019082 | GCUGAACUGGGCUGAGCUGGGC | SEQ ID NO: 11 |
| hsa-miR-631 | MIMAT0003300 | AGACCUGGCCCAGACCUCAGC | SEQ ID NO: 12 |
| hsa-miR-766-3p | MIMAT0003888 | ACUCCAGCCCCACAGCCUCAGC | SEQ ID NO: 13 |
| hsa-miR-3940-5p | MIMAT0019229 | GUGGGUUGGGCGGGCUCUG | SEQ ID NO: 14 |
| hsa-miR-3200-5p | MIMAT0017392 | AAUCUGAGAAGGCGCACAAGGU | SEQ ID NO: 15 |
| hsa-let-7c-5p | MIMAT0000064 | UGAGGUAGUAGGUUGUAUGGUU | SEQ ID NO: 16 |
| hsa-miR-29a-3p | MIMAT0000086 | UAGCACCAUCUGAAAUCGGUUA | SEQ ID NO: 17 |
| hsa-miR-1537-3p | MIMAT0007399 | AAAACCGUCUAGUUACAGUUGU | SEQ ID NO: 18 |
| hsa-miR-4505 | MIMAT0019041 | AGGCUGGGCUGGGACGGA | SEQ ID NO: 19 |
| hsa-miR-93-3p | MIMAT0004509 | ACUGCUGAGCUAGCACUUCCCG | SEQ ID NO: 20 |
| hsa-miR-15b-3p | MIMAT0004586 | CGAAUCAUUAUUUGCUGCUCUA | SEQ ID NO: 21 |
| hsa-miR-663a | MIMAT0003326 | AGGCGGGGCGCCGCGGGACCGC | SEQ ID NO: 22 |
| hsa-let-7b-5p | MIMAT0000063 | UGAGGUAGUAGGUUGUGUGGUU | SEQ ID NO: 23 |
| hsa-miR-21-5p | MIMAT0000076 | UAGCUUAUCAGACUGAUGUUGA | SEQ ID NO: 24 |
| hsa-miR-1909-5p | MIMAT0007882 | UGAGUGCCGGUGCCUGCCCUG | SEQ ID NO: 25 |
| hsa-miR-4446-3p | MIMAT0018965 | CAGGGCUGGCAGUGACAUGGGU | SEQ ID NO: 26 |
| hsa-miR-373-5p | MIMAT0000725 | ACUCAAAAUGGGGGCGCUUUCC | SEQ ID NO: 27 |

REFERENCES

1. Mauer S M, Steffes M W, Ellis E N, Sutherland D E, Brown D M, Goetz F C: Structural-functional relationships in diabetic nephropathy. J Clin Invest 1984; 74:1143-1155
2. Krolewski A S, Gohda T, Niewczas M A: Progressive renal decline as the major feature of diabetic nephropathy in type 1 diabetes. Clin Exp Nephrol 2014; 18:571-583
3. Yamamoto T, Nakamura T, Noble N A, Ruoslahti E, Border W A: Expression of transforming growth factor beta is elevated in human and experimental diabetic nephropathy. Proceedings of the National Academy of Sciences of the United States of America 1993; 90:1814-1818
4. Sharma K, Ziyadeh F N: Hyperglycemia and diabetic kidney disease. The case for transforming growth factor-beta as a key mediator. Diabetes 1995; 44:1139-1146
5. Sharma K, Ziyadeh F N, Alzahabi B, McGowan T A, Kapoor S, Kurnik B R, Kurnik P B, Weisberg L S: Increased renal production of transforming growth factor-beta1 in patients with type II diabetes. Diabetes 1997; 46:854-859
6. Hayashida T, Poncelet A C, Hubchak S C, Schnaper H W: TGF-beta1 activates MAP kinase in human mesangial cells: a possible role in collagen expression. Kidney Int 1999; 56:1710-1720
7. Poncelet A C, Schnaper H W: Sp1 and Smad proteins cooperate to mediate transforming growth factor-beta 1-induced alpha 2(I) collagen expression in human glomerular mesangial cells. The Journal of biological chemistry 2001; 276:6983-6992
8. Chin B Y, Mohsenin A, Li S X, Choi A M, Choi M E: Stimulation of pro-alpha(1)(I) collagen by TGF-beta(1) in mesangial cells: role of the p38 MAPK pathway. Am J Physiol Renal Physiol 2001; 280:F495-504
9. Tsuchida K, Zhu Y, Siva S, Dunn S R, Sharma K: Role of Smad4 on TGF-beta-induced extracellular matrix stimulation in mesangial cells. Kidney Int 2003; 63:2000-2009
10. Du B, Ma L M, Huang M B, Zhou H, Huang H L, Shao P, Chen Y Q, Qu L H: High glucose down-regulates miR-29a to increase collagen IV production in HK-2 cells. FEBS Lett 2010; 584:811-816
11. Kato M, Zhang J, Wang M, Lanting L, Yuan H, Rossi J J, Natarajan R: MicroRNA-192 in diabetic kidney glomeruli and its function in TGF-beta-induced collagen expression via inhibition of E-box repressors. Proceedings of the National Academy of Sciences of the United States of America 2007; 104:3432-3437
12. Kriegel A J, Liu Y, Cohen B, Usa K, Liu Y, Liang M: MiR-382 targeting of kallikrein 5 contributes to renal inner medullary interstitial fibrosis. Physiol Genomics 2012; 44:259-267
13. Krupa A, Jenkins R, Luo D D, Lewis A, Phillips A, Fraser D: Loss of MicroRNA-192 promotes fibrogenesis in diabetic nephropathy. J Am Soc Nephrol 2010; 21:438-447
14. Putta S, Lanting L, Sun G, Lawson G, Kato M, Natarajan R: Inhibiting microRNA-192 ameliorates renal fibrosis in diabetic nephropathy. J Am Soc Nephrol 2012; 23:458-469
15. Wang J, Gao Y, Ma M, Li M, Zou D, Yang J, Zhu Z, Zhao X: Effect of miR-21 on renal fibrosis by regulating MMP-9 and TIMP1 in kk-ay diabetic nephropathy mice. Cell Biochem Biophys 2013; 67:537-546
16. Wang J Y, Gao Y B, Zhang N, Zou D W, Wang P, Zhu Z Y, Li J Y, Zhou S N, Wang S C, Wang Y Y, Yang J K: miR-21 overexpression enhances TGF-beta1-induced epithelial-to-mesenchymal transition by target smad7 and aggravates renal damage in diabetic nephropathy. Mol Cell Endocrinol 2014; 392:163-172
17. Wang Q, Wang Y, Minto A W, Wang J, Shi Q, Li X, Quigg R J: MicroRNA-377 is up-regulated and can lead to increased fibronectin production in diabetic nephropathy. FASEB J 2008; 22:4126-4135
18. Zhong X, Chung A C, Chen H Y, Dong Y, Meng X M, Li R, Yang W, Hou F F, Lan H Y: miR-21 is a key therapeutic target for renal injury in a mouse model of type 2 diabetes. Diabetologia 2013; 56:663-674

19. Mitchell P S, Parkin R K, Kroh E M, Fritz B R, Wyman S K, Pogosova-Agadjanyan E L, Peterson A, Noteboom J, O'Briant K C, Allen A, Lin D W, Urban N, Drescher C W, Knudsen B S, Stirewalt D L, Gentleman R, Vessella R L, Nelson P S, Martin D B, Tewari M: Circulating microRNAs as stable blood-based markers for cancer detection. Proceedings of the National Academy of Sciences of the United States of America 2008; 105:10513-10518

20. Weber J A, Baxter D H, Zhang S, Huang D Y, Huang K H, Lee M J, Galas D J, Wang K: The microRNA spectrum in 12 body fluids. Clin Chem 2010; 56:1733-1741

21. Fichtlscherer S, De Rosa S, Fox H, Schwietz T, Fischer A, Liebetrau C, Weber M, Hamm C W, Roxe T, Muller-Ardogan M, Bonauer A, Zeiher A M, Dimmeler S: Circulating microRNAs in patients with coronary artery disease. Circ Res 2010; 107:677-684

22. Heegaard N H, Schetter A J, Welsh J A, Yoneda M, Bowman E D, Harris C C: Circulating micro-RNA expression profiles in early stage nonsmall cell lung cancer. Int J Cancer 2012; 130:1378-1386

23. DiStefano J K, Taila M, Alvarez M L: Emerging roles for miRNAs in the development, diagnosis, and treatment of diabetic nephropathy. Curr Diab Rep 2013; 13:582-591

24. Argyropoulos C, Wang K, McClarty S, Huang D, Bernardo J, Ellis D, Orchard T, Galas D, Johnson J: Urinary microRNA profiling in the nephropathy of type 1 diabetes. PloS one 2013; 8:e54662

25. Barutta F, Tricarico M, Corbelli A, Annaratone L, Pinach S, Grimaldi S, Bruno G, Cimino D, Taverna D, Deregibus M C, Rastaldi M P, Perin P C, Gruden G: Urinary exosomal microRNAs in incipient diabetic nephropathy. PloS one 2013; 8:e73798

26. Peng H, Zhong M, Zhao W, Wang C, Zhang J, Liu X, Li Y, Paudel S D, Wang Q, Lou T: Urinary miR-29 correlates with albuminuria and carotid intima-media thickness in type 2 diabetes patients. PloS one 2013; 8:e82607

27. He F, Peng F, Xia X, Zhao C, Luo Q, Guan W, Li Z, Yu X, Huang F: MiR-135a promotes renal fibrosis in diabetic nephropathy by regulating TRPC1. Diabetologia 2014; 57:1726-1736

28. Zhang C, Zhang W, Chen H M, Liu C, Wu J, Shi S, Liu Z H: Plasma MicroRNA-186 and Proteinuria in Focal Segmental Glomerulosclerosis. American journal of kidney diseases: the official journal of the National Kidney Foundation 2014;

29. Rosolowsky E T, Skupien J, Smiles A M, Niewczas M, Roshan B, Stanton R, Eckfeldt J H, Warram J H, Krolewski A S: Risk for ESRD in type 1 diabetes remains high despite renoprotection. J Am Soc Nephrol 2011; 22:545-553

30. Skupien J, Warram J H, Smiles A M, Niewczas M A, Gohda T, Pezzolesi M G, Cantarovich D, Stanton R, Krolewski A S: The early decline in renal function in patients with type 1 diabetes and proteinuria predicts the risk of end-stage renal disease. Kidney Int 2012; 82:589-597

31. Levey A S, Stevens L A, Schmid C H, Zhang Y L, Castro A F, 3rd, Feldman H I, Kusek J W, Eggers P, Van Lente F, Greene T, Coresh J, Ckd EPI: A new equation to estimate glomerular filtration rate. Ann Intern Med 2009; 150:604-612

32. Krolewski A S, Niewczas M A, Skupien J, Gohda T, Smiles A, Eckfeldt J H, Doria A, Warram J H: Early progressive renal decline precedes the onset of microalbuminuria and its progression to macroalbuminuria. Diabetes Care 2014; 37:226-234

33. Arroyo J D, Chevillet J R, Kroh E M, Ruf 1K, Pritchard C C, Gibson D F, Mitchell P S, Bennett C F, Pogosova-Agadjanyan E L, Stirewalt D L, Tait J F, Tewari M: Argonaute2 complexes carry a population of circulating microRNAs independent of vesicles in human plasma. Proceedings of the National Academy of Sciences of the United States of America 2011; 108:5003-5008

34. Kroh E M, Parkin R K, Mitchell P S, Tewari M: Analysis of circulating microRNA biomarkers in plasma and serum using quantitative reverse transcription-PCR (qRT-PCR). Methods 2010; 50:298-301

35. Brennan E P, Nolan K A, Borgeson E, Gough O S, McEvoy C M, Docherty N G, Higgins D F, Murphy M, Sadlier D M, Ali-Shah S T, Guiry P J, Savage D A, Maxwell A P, Martin F, Godson C, Consortium G: Lipoxins attenuate renal fibrosis by inducing let-7c and suppressing TGFbetaR1. J Am Soc Nephrol 2013; 24:627-637

36. Deshpande S D, Putta S, Wang M, Lai J Y, Bitzer M, Nelson R G, Lanting L L, Kato M, Natarajan R: Transforming growth factor-beta-induced cross talk between p53 and a microRNA in the pathogenesis of diabetic nephropathy. Diabetes 2013; 62:3151-3162

37. Dey N, Ghosh-Choudhury N, Kasinath B S, Choudhury G G: TGFbeta-stimulated microRNA-21 utilizes PTEN to orchestrate AKT/mTORC1 signaling for mesangial cell hypertrophy and matrix expansion. PloS one 2012; 7:e42316

38. Kato M, Arce L, Wang M, Putta S, Lanting L, Natarajan R: A microRNA circuit mediates transforming growth factor-beta1 autoregulation in renal glomerular mesangial cells. Kidney Int 2011; 80:358-368

39. Kato M, Natarajan R: Diabetic nephropathy—emerging epigenetic mechanisms. Nat Rev Nephrol 2014; 10:517-530

40. Qin W, Chung A C, Huang X R, Meng X M, Hui D S, Yu C M, Sung J J, Lan H Y: TGF-beta/Smad3 signaling promotes renal fibrosis by inhibiting miR-29. J Am Soc Nephrol 2011; 22:1462-1474

41. van Rooij E, Sutherland L B, Thatcher J E, DiMaio J M, Naseem R H, Marshall W S, Hill J A, Olson E N: Dysregulation of microRNAs after myocardial infarction reveals a role of miR-29 in cardiac fibrosis. Proceedings of the National Academy of Sciences of the United States of America 2008; 105:13027-13032

42. Wang B, Herman-Edelstein M, Koh P, Burns W, Jandeleit-Dahm K, Watson A, Saleem M, Goodall G J, Twigg S M, Cooper M E, Kantharidis P: E-cadherin expression is regulated by miR-192/215 by a mechanism that is independent of the profibrotic effects of transforming growth factor-beta. Diabetes 2010; 59:1794-1802

43. Wang B, Komers R, Carew R, Winbanks C E, Xu B, Herman-Edelstein M, Koh P, Thomas M, Jandeleit-Dahm K, Gregorevic P, Cooper M E, Kantharidis P: Suppression of microRNA-29 expression by TGF-beta1 promotes collagen expression and renal fibrosis. J Am Soc Nephrol 2012; 23:252-265

44. Zhou Q, Fan J, Ding X, Peng W, Yu X, Chen Y, Nie J: TGF-{beta}-induced MiR-491-5p expression promotes Par-3 degradation in rat proximal tubular epithelial cells. The Journal of biological chemistry 2010; 285:40019-40027

45. Zhong X, Chung A C, Chen H Y, Meng X M, Lan H Y: Smad3-mediated upregulation of miR-21 promotes renal fibrosis. J Am Soc Nephrol 2011; 22:1668-1681

46. Schaeffer V, Hansen K M, Morris D R, LeBoeuf R C, Abrass C K: RNA-binding protein IGF2BP2/IMP2 is required for laminin-beta2 mRNA translation and is modulated by glucose concentration. Am J Physiol Renal Physiol 2012; 303:F75-82

47. Pawing H H, Mauer M, Ritz E: Diabetic nephropathy. In The Kidney, 7th ed. Brenner B M, Ed. Philadelphia, Elsevier, 2004, p. 1777-1818

48. Long J, Wang Y, Wang W, Chang B H, Danesh F R: MicroRNA-29c is a signature microRNA under high glucose conditions that targets Sprouty homolog 1, and its in vivo knockdown prevents progression of diabetic nephropathy. The Journal of biological chemistry 2011; 286: 11837-11848

49. Turchinovich A, Weiz L, Langheinz A, Burwinkel B: Characterization of extracellular circulating microRNA. Nucleic Acids Res 2011; 39:7223-7233

50. Tian Z, Greene A S, Pietrusz J L, Matus I R, Liang M: MicroRNA-target pairs in the rat kidney identified by microRNA microarray, proteomic, and bioinformatic analysis. Genome Res 2008; 18:404-411

The invention claimed is:

1. A method for identifying a subject who is at risk of developing end-stage renal disease (ESRD), said method comprising determining the relative level of a progressor miRNA selected from the group consisting of let-7b-5p and miR-21-5p in a sample from the subject, wherein a higher level of the progressor mRNA in comparison to either a non-progressor control level of the progressor miRNA or a normoalbuminuric control level of the progressor mi RNA indicates that the subject is at risk of developing ESRD, further comprising administering to the subject an antagonist of let-7b-5p and/or mi R-21-5p if the subject is at risk of developing ESRD.

2. The method of claim 1, further comprising administering to the subject a renal protective agent if the subject is at risk of developing ESRD.

3. The method of claim 1, wherein the subject has diabetes or high blood pressure.

4. The method of claim 1, wherein the sample is a plasma sample.

5. The method of claim 1, wherein the level of the miRNA is determined using quantitative PCR (qPCR), hybridization analysis, or microarray analysis.

6. The method of claim 1, wherein the sample comprises blood constituents.

7. The method of claim 1, further comprising determining the relative level of a protective miRNA in the sample from the subject, wherein a decrease in the level of the protective miRNA in comparison to either a non-progressor control level of the protective miRNA or a normoalbuminuric control level of the protective miRNA indicates that the subject is at risk of developing ESRD.

8. The method of claim 7, wherein the protective miRNA is let-7c-5p and/or miR-29a-3p.

9. A method for identifying a subject who is at risk of developing end-stage renal disease (ESRD), said method comprising determining the relative level of a protective miRNA selected from the group consisting of let-7c-5p and miR-29a-3p in a sample from the subject, wherein a decrease in the level of the protective miRNA in comparison to either a non-progressor control level of the protective miRNA or a normoalbuminuric control level of the protective miRNA indicates that the subject is at risk of developing ESRD, further comprising administering to the subject a therapeutically effective amount of a protective miRNA agent, if the subject is at risk of developing ESRD.

10. The method of claim 9, wherein the protective miRNA agent is selected from the group consisting of a let-7c-5p, a let-7c-5p mimic, a synthetic let-7c-5p oligonucleotide, and an expression vector encoding let-7c-5p.

11. The method of claim 9, wherein the protective miRNA agent is selected from the group consisting of a miR-29a-3p, a miR-29a-3p mimic, a synthetic miR-29a-3p oligonucleotide, and an expression vector encoding miR-29a-3p.

12. The method of claim 9, further comprising administering to the subject a renal protective agent if the subject is at risk of developing ESRD.

* * * * *

SEQUENCE LISTING

```
<160> NUMBER OF SEQ ID NOS: 27

<210> SEQ ID NO 1
<211> LENGTH: 23
<212> TYPE: RNA
<213> ORGANISM: Homo sapiens

<400> SEQUENCE: 1
uacccuguag aaccgaauuu gug                                              23

<210> SEQ ID NO 2
<211> LENGTH: 22
<212> TYPE: RNA
<213> ORGANISM: Homo sapiens

<400> SEQUENCE: 2
aaaccguuac cauuacugag uu                                               22

<210> SEQ ID NO 3
<211> LENGTH: 23
<212> TYPE: RNA
<213> ORGANISM: Homo sapiens

<400> SEQUENCE: 3
cccaguguuc agacuaccug uuc                                              23

<210> SEQ ID NO 4
<211> LENGTH: 22
<212> TYPE: RNA
<213> ORGANISM: Homo sapiens

<400> SEQUENCE: 4
aggugcucca ggcuggcuca ca                                               22

<210> SEQ ID NO 5
<211> LENGTH: 21
<212> TYPE: RNA
<213> ORGANISM: Homo sapiens

<400> SEQUENCE: 5
ugagaugaag cacuguagcu c                                                21

<210> SEQ ID NO 6
<211> LENGTH: 23
<212> TYPE: RNA
<213> ORGANISM: Homo sapiens

<400> SEQUENCE: 6
ugugcaaauc caugcaaaac uga                                              23

<210> SEQ ID NO 7
<211> LENGTH: 22
<212> TYPE: RNA
```

```
<213> ORGANISM: Homo sapiens

<400> SEQUENCE: 7
aguucuucag uggcaagcuu ua                                              22

<210> SEQ ID NO 8
<211> LENGTH: 23
<212> TYPE: RNA
<213> ORGANISM: Homo sapiens

<400> SEQUENCE: 8
agcuacauug ucugcugggu uuc                                             23

<210> SEQ ID NO 9
<211> LENGTH: 23
<212> TYPE: RNA
<213> ORGANISM: Homo sapiens

<400> SEQUENCE: 9
agcuacauug ucugcugggu uuc                                             23

<210> SEQ ID NO 10
<211> LENGTH: 20
<212> TYPE: RNA
<213> ORGANISM: Homo sapiens

<400> SEQUENCE: 10 cugguuggg cugggcuggg                                                  20

<210> SEQ ID NO 11
<211> LENGTH: 22
<212> TYPE: RNA
<213> ORGANISM: Homo sapiens

<400> SEQUENCE: 11
gcugaacugg gcugagcugg gc                                              22

<210> SEQ ID NO 12
<211> LENGTH: 21
<212> TYPE: RNA
<213> ORGANISM: Homo sapiens

<400> SEQUENCE: 12
agaccuggcc cagaccucag c                                               21

<210> SEQ ID NO 13
<211> LENGTH: 22
<212> TYPE: RNA
<213> ORGANISM: Homo sapiens

<400> SEQUENCE: 13
acuccagccc cacagccuca gc                                              22

<210> SEQ ID NO 14
<211> LENGTH: 20
<212> TYPE: RNA
<213> ORGANISM: Homo sapiens

<400> SEQUENCE: 14 gugguuggg gcgggcucug                                                  20

<210> SEQ ID NO 15
<211> LENGTH: 22
```

<212> TYPE: RNA
<213> ORGANISM: Homo sapiens

<400> SEQUENCE: 15
aaucugagaa ggcgcacaag gu                                          22

<210> SEQ ID NO 16
<211> LENGTH: 22
<212> TYPE: RNA
<213> ORGANISM: Homo sapiens

<400> SEQUENCE: 16
ugagguagua gguuguaugg uu                                          22

<210> SEQ ID NO 17
<211> LENGTH: 22
<212> TYPE: RNA
<213> ORGANISM: Homo sapiens

<400> SEQUENCE: 17
uagcaccauc ugaaaucggu ua                                          22

<210> SEQ ID NO 18
<211> LENGTH: 22
<212> TYPE: RNA
<213> ORGANISM: Homo sapiens

<400> SEQUENCE: 18
aaaaccgucu aguuacaguu gu                                          22

<210> SEQ ID NO 19
<211> LENGTH: 18
<212> TYPE: RNA
<213> ORGANISM: Homo sapiens

<400> SEQUENCE: 19
aggcugggcu gggacgga                                               18

<210> SEQ ID NO 20
<211> LENGTH: 22
<212> TYPE: RNA
<213> ORGANISM: Homo sapiens

<400> SEQUENCE: 20
acugcugagc uagcacuucc cg                                          22

<210> SEQ ID NO 21
<211> LENGTH: 22
<212> TYPE: RNA
<213> ORGANISM: Homo sapiens

<400> SEQUENCE: 21
cgaaucauua uuugcugcuc ua                                          22

<210> SEQ ID NO 22
<211> LENGTH: 22
<212> TYPE: RNA
<213> ORGANISM: Homo sapiens

<400> SEQUENCE: 22
aggcggggcg ccgcgggacc gc                                          22

<210> SEQ ID NO 23

```
<211> LENGTH: 22
<212> TYPE: RNA
<213> ORGANISM: Homo sapiens

<400> SEQUENCE: 23
ugagguagua gguugugugg uu                                               22

<210> SEQ ID NO 24
<211> LENGTH: 22
<212> TYPE: RNA
<213> ORGANISM: Homo sapiens

<400> SEQUENCE: 24
uagcuuauca gacugauguu ga                                               22

<210> SEQ ID NO 25
<211> LENGTH: 21
<212> TYPE: RNA
<213> ORGANISM: Homo sapiens

<400> SEQUENCE: 25
ugagugccgg ugccugcccu g                                                21

<210> SEQ ID NO 26
<211> LENGTH: 22
<212> TYPE: RNA
<213> ORGANISM: Homo sapiens

<400> SEQUENCE: 26
cagggcuggc agugacaugg gu                                               22

<210> SEQ ID NO 27
<211> LENGTH: 22
<212> TYPE: RNA
<213> ORGANISM: Homo sapiens

<400> SEQUENCE: 27
acucaaaaug ggggcgcuuu cc                                               22
```